United States Patent
Ho et al.

(10) Patent No.: US 10,119,117 B2
(45) Date of Patent: Nov. 6, 2018

(54) UNIVERSAL, GLYCOSYLATION ENHANCER, COMPLETELY CHEMICALLY DEFINED MEDIUM FORMULATION

(71) Applicant: Nanogen Pharmaceutical Biotechnology Co., Ltd, Ho Chi Minh (VN)

(72) Inventors: Nhan Ho, Ho Chi Minh (VN); Praveen Gupta, Ho Chi Minh (VN); Si Minh Do, Ho Chi Minh (VN); Phuong Thi Bich Ho, Ho Chi Minh (VN); Ngoc-Thuy Bui, Ho Chi Minh (VN); Huy Quang Nguyen, Ho Chi Minh (VN); Trang Thi Thuy Nguyen, Ho Chi Minh (VN); Ha Thi Hong Truong, Ho Chi Minh (VN); Tuan Anh Le, Ho Chi Minh (VN)

(73) Assignee: NANOGEN PHARMACEUTICAL BIOTECHNOLOGY CO., LTD, Ho Chi Minh (VN)

( * ) Notice: Subject to any disclaimer, the term of this patent is extended or adjusted under 35 U.S.C. 154(b) by 64 days.

(21) Appl. No.: 15/404,007

(22) Filed: Jan. 11, 2017

(65) Prior Publication Data
US 2017/0218328 A1 Aug. 3, 2017

Related U.S. Application Data

(60) Provisional application No. 62/288,139, filed on Jan. 28, 2016.

(51) Int. Cl.
*C12N 5/00* (2006.01)

(52) U.S. Cl.
CPC ........ *C12N 5/0018* (2013.01); *C12N 2500/32* (2013.01); *C12N 2500/34* (2013.01); *C12N 2500/38* (2013.01); *C12N 2500/40* (2013.01); *C12N 2500/60* (2013.01)

(58) Field of Classification Search
None
See application file for complete search history.

(56) References Cited

U.S. PATENT DOCUMENTS

| | | | |
|---|---|---|---|
| 4,786,599 A | 11/1988 | Chessebeuf et al. | |
| 4,816,401 A | 3/1989 | Taupier et al. | |
| 4,927,762 A | 5/1990 | Darfler | |
| 5,045,454 A | 9/1991 | Bertheussen | |
| 5,045,467 A | 9/1991 | Bertheussen | |
| 5,633,162 A | 5/1997 | Keen et al. | |
| 5,661,034 A * | 8/1997 | Hayakawa | C07K 14/8146 435/347 |
| 5,707,832 A | 1/1998 | Mignot et al. | |
| 5,712,163 A | 1/1998 | Parenteau et al. | |
| 6,048,728 A | 4/2000 | Inlow et al. | |
| 6,656,719 B1 * | 12/2003 | Gould | A61K 39/15 424/184.1 |
| 7,601,535 B1 | 10/2009 | Weng et al. | |
| 9,068,970 B2 * | 6/2015 | Hossler | G01N 33/5008 |

OTHER PUBLICATIONS

Chaproniere-Rickenberg et al., "Zinc Levels in Zinc-Stabilized Insulin are Inhibitory to the Growth of Cells in Vitro" In Vitro 19:373-375, Tissue Culture Assn. 1983.
Gramer, M.I. et al.,"Removal of Sialic Acid from a Gylcoprotein in CHO Cell Culture Supernatant by Action . . . " Biotechnol. 13:692-698, Butterworth-Heinemann (Jul. 1995).
Schlager, E.-J. "The protein hydrolysate, Primatone RL is a cost effective multiple growth promoter . . . " J Immunol. Meth. 194:191-199, North-Holland Publ Co. Aug. 1996.
Ezaki, O. "IIb Group Metal Ions (Zn+2, Cd+2, and Hg+2) Stimulate Glucose Transport Activity by Post-insulin Receptor Kinase . . . "J. Biol. Chem. vol. 264, (1989) pp. 16118-16122.
Tang, X-H. and Shay, NF. "Zinc Has an Insulin-like Effect on Glucose Transport Mediated by . . . " J. Nutrit., vol. 131, (2001), pp. 1414-1420.
Waymouth, C. "Osmolality of Mammalian Blood and of Media for Culture of Mammalian Cells" In Vitro 6:109-127, Tissue Culture Assn. (1970).

(Continued)

*Primary Examiner* — David W Berke-Schlessel
(74) *Attorney, Agent, or Firm* — Sam L. Nguyen; Hamilton DeSanctis & Cha, LLP

(57) ABSTRACT

In one embodiment, the present application discloses a cell culture medium for culturing cell lines suitable for producing a therapeutic protein, comprising an amino acid selected from a group consisting of L-arginine, L-asparagine, L-proline, L leucine and L hydroxyproline and a mixture thereof; a vitamin selected from a group consisting of ascorbic acid $Mg^{2+}$ salt, biotin, pyridoxine HCL, folic acid, riboflavin and D-calcium pantothenate, and a mixture thereof; an element selected from a group consisting of ammonium meta vanadate, sodium meta vanadate, germanium dioxide, barium acetate, aluminum chloride, rubidium chloride, cadmium chloride, ammonium molybedate, stannous chloride, cobalt chloride, chromium sulfate, silver nitrate, sodium metasilicate, zinc sulfate, manganese sulfate $H_2O$, manganous chloride, ferric nitrate $9H_2O$, ferrous sulfate $7H_2O$, ferric ammonium citrate, magnesium chloride anhydrous, and magnesium sulfate anhydrous, and a mixture thereof; a nucleoside selected from a group consisting of uridine and cystidine; a sugar selected from a group consisting of galactose, mannose and N-Acetyl-D-Mannosamine; and a triple buffering system comprising sodium carbonate, sodium bicarbonate and HEPES; wherein the cell culture medium is animal component-free, plant component-free, serum-free, growth factors-free, recombinant protein-free, lipid-free, steroid-free, and free of plant or animal hydrolysates and/or extracts.

15 Claims, 10 Drawing Sheets

(56) References Cited

OTHER PUBLICATIONS

Ronit, Iiouz et al, "Inhibition of glycogen synthase kinase-3b by bivalent zinc ions: insight into . . . " Biochemical and Biophysical Research Communications 295 (2002) 102-106.
Shiro Bannai "Effect of Cystine Depletion on Growth-Arrested Human Diploid Fibroblasts" ELL Structure and Function 4, 109-115 (1979).

* cited by examiner

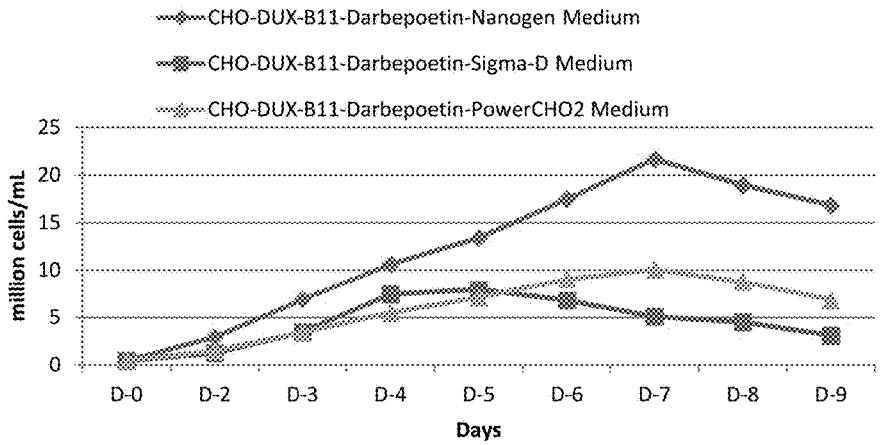
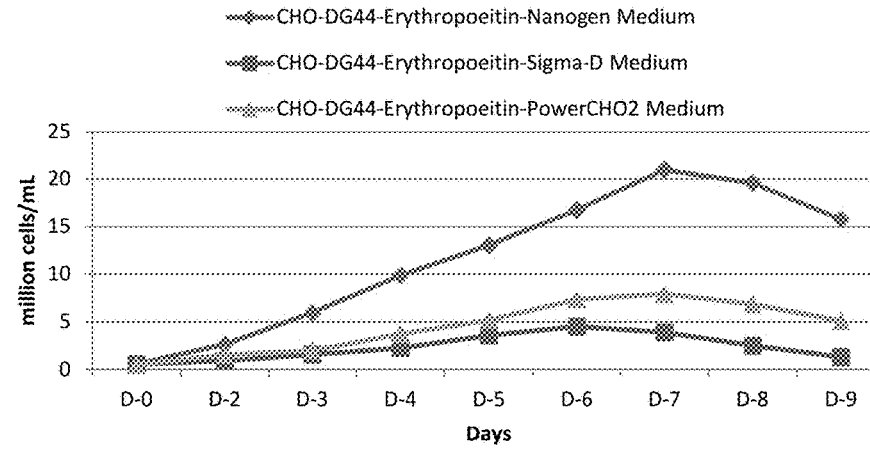

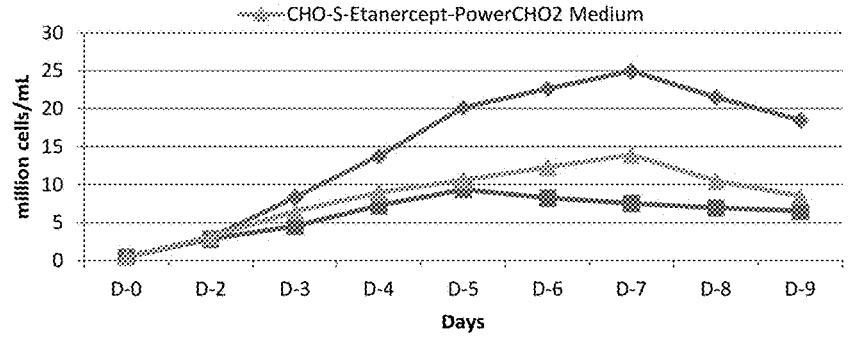
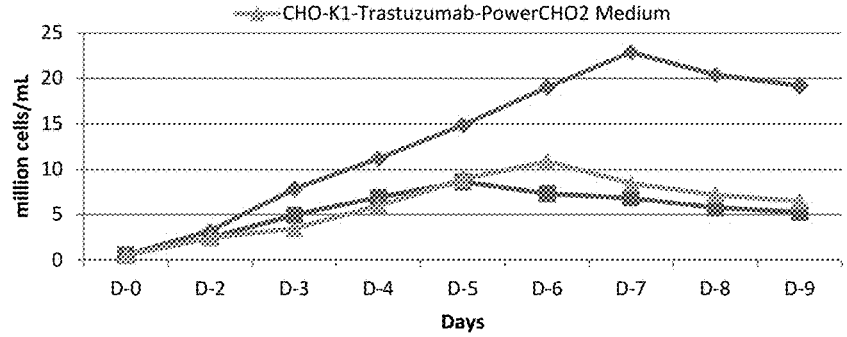

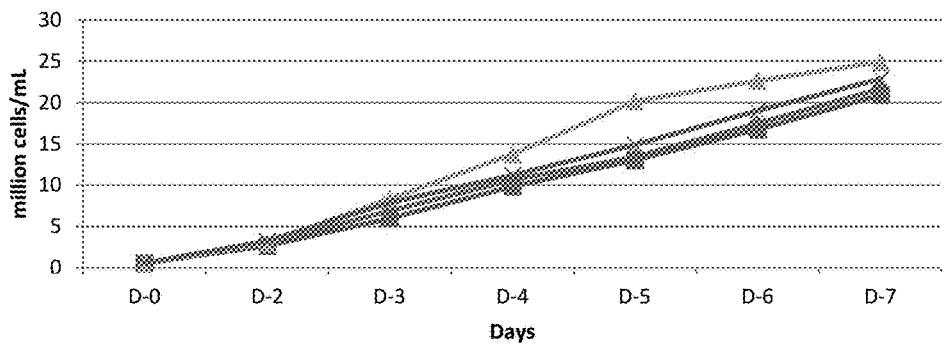
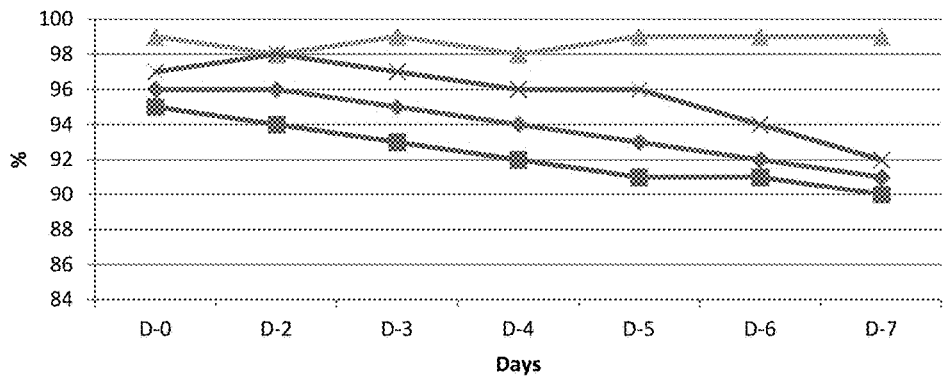

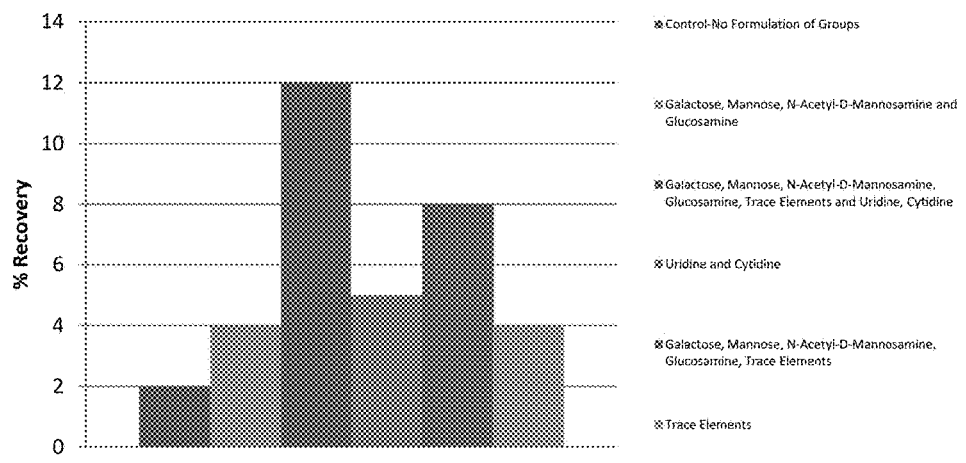
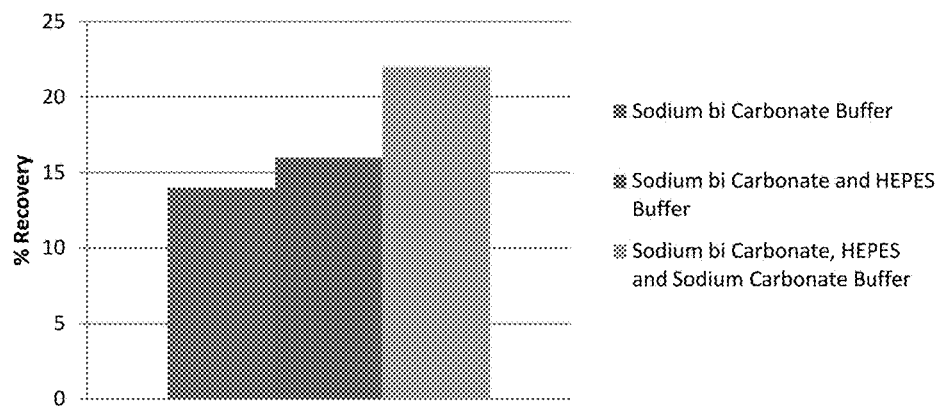

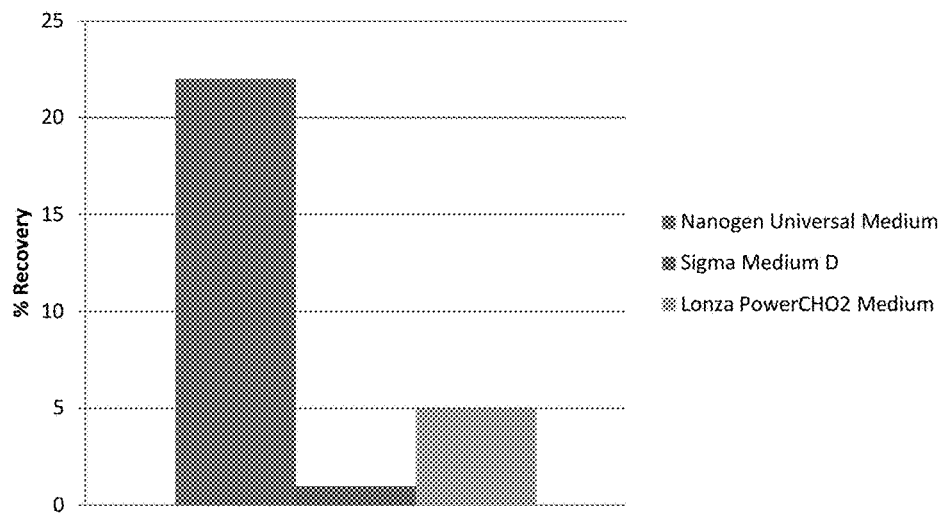
Fig. 9- Protein recovery after purification in Universal Production Medium at shake flask scale recombinant CHO-DG44-Erythropoeitin
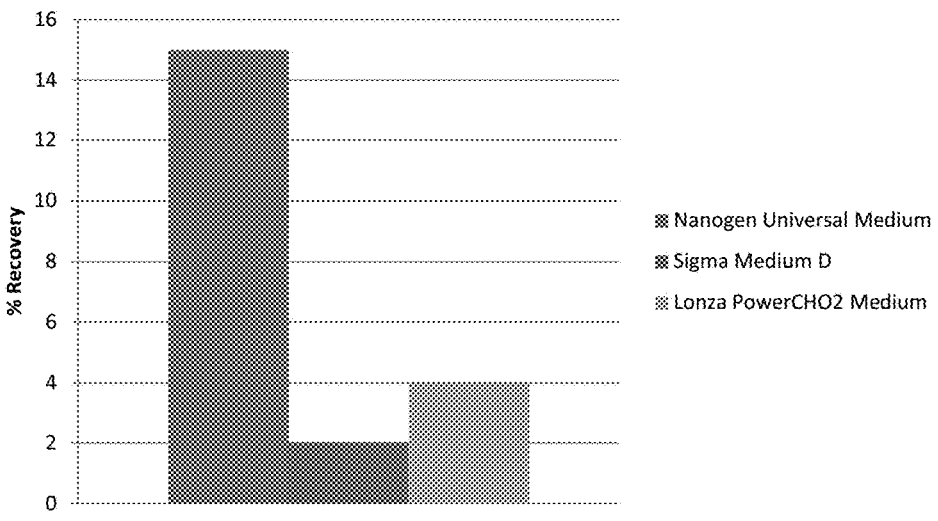
Fig. 10- Protein recovery after purification in Universal Production medium at shake flask scale recombinant CHO-Dux-B11-Darbepoetin

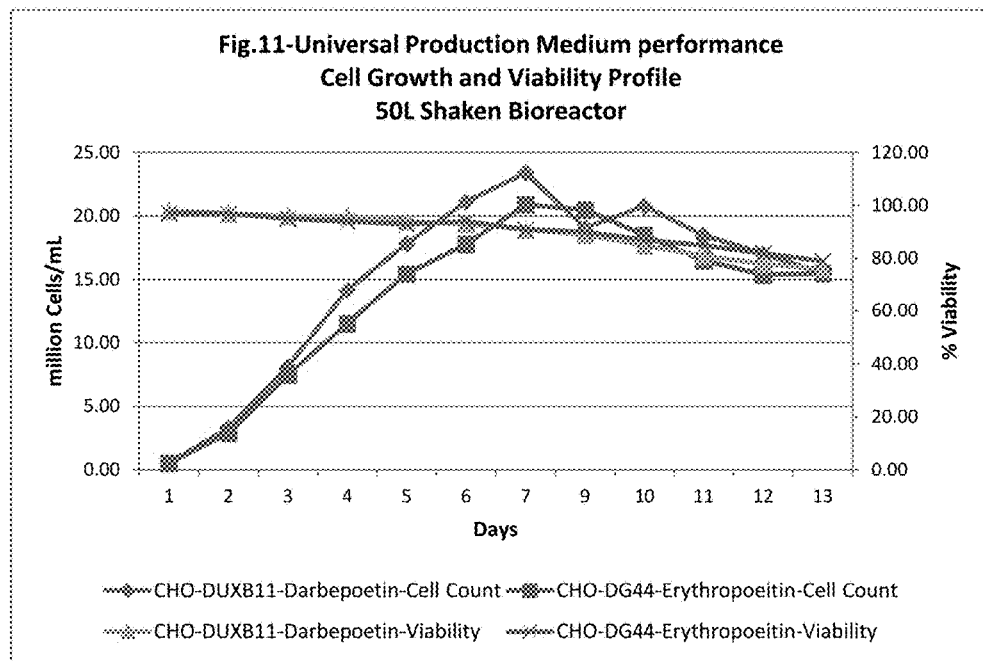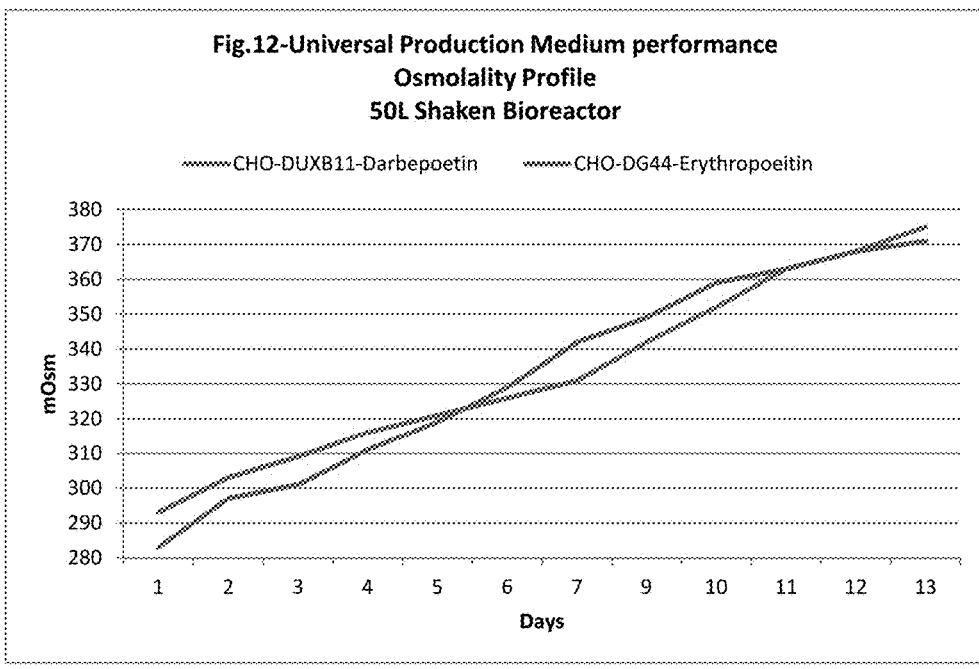

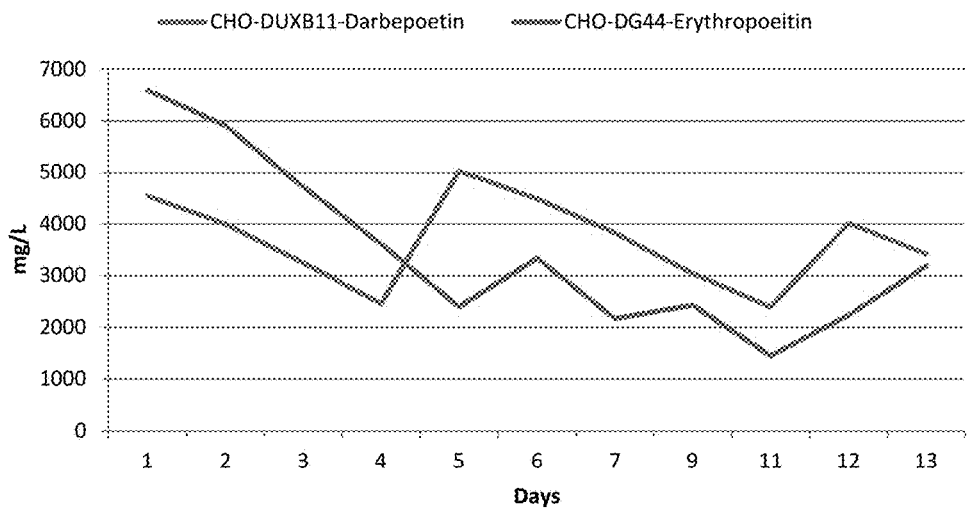
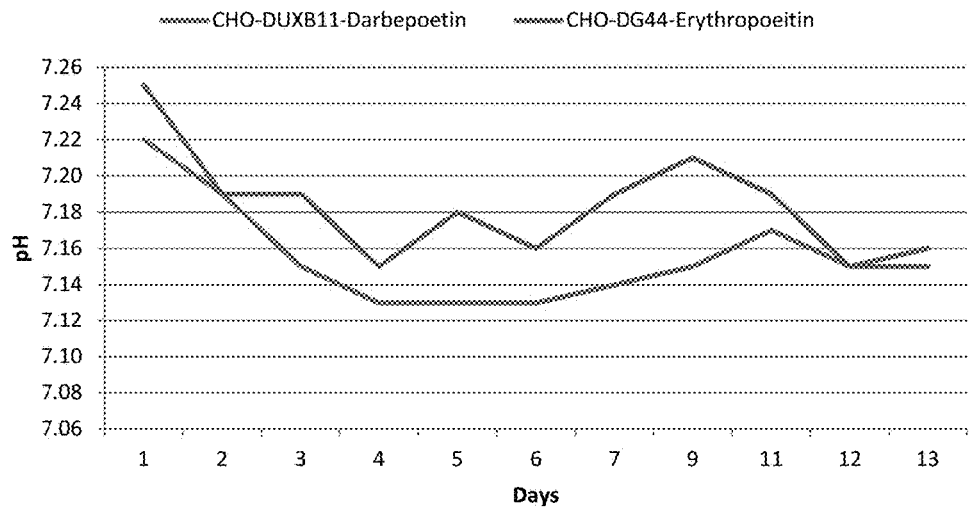

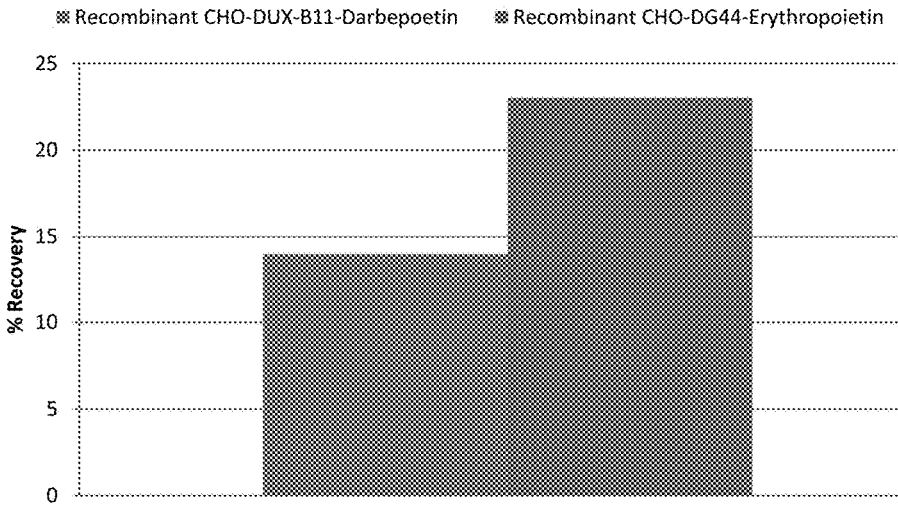
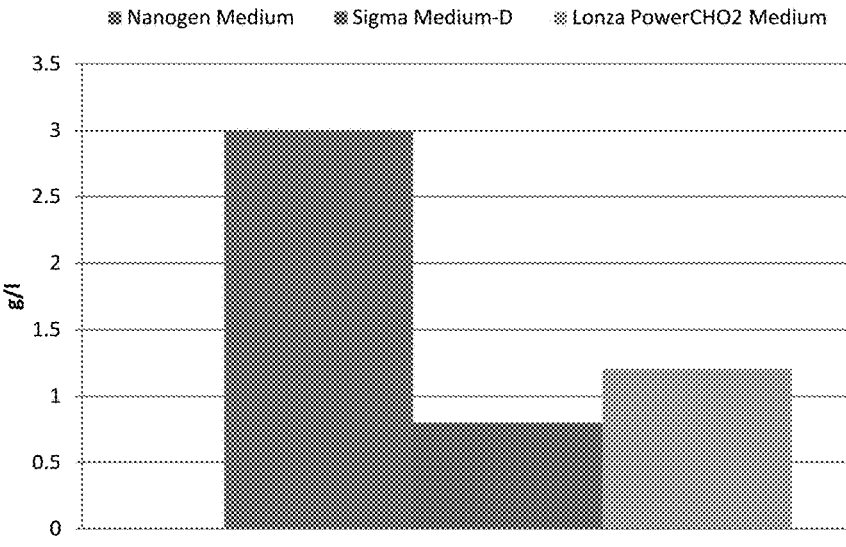

Fig. 17. Universal Medium Performance in Fed Batch Culture at 50 L Scale
Image.1-Iso Electric Focusing DARBEPOETIN ALFA
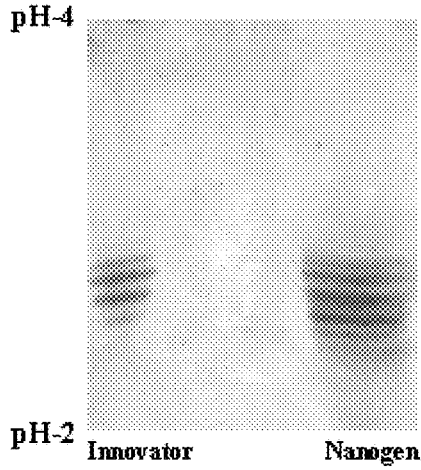
Gel pH-4
pH-2  Innovator   Nanogen
Fig. 18. Universal Medium Performance in Fed Batch Culture at 50 L Scale
Image .2-Iso Electric Focusing ERYTHROPOIETIN
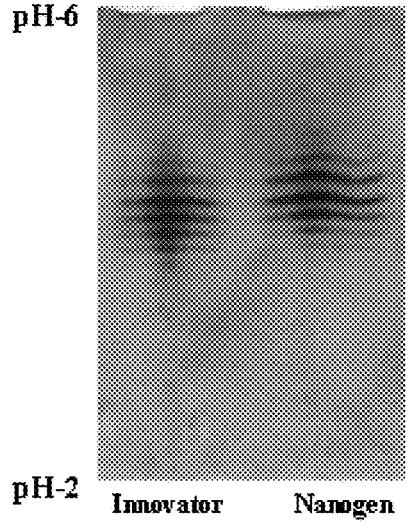
Gel pH-6
pH-2  Innovator   Nanogen

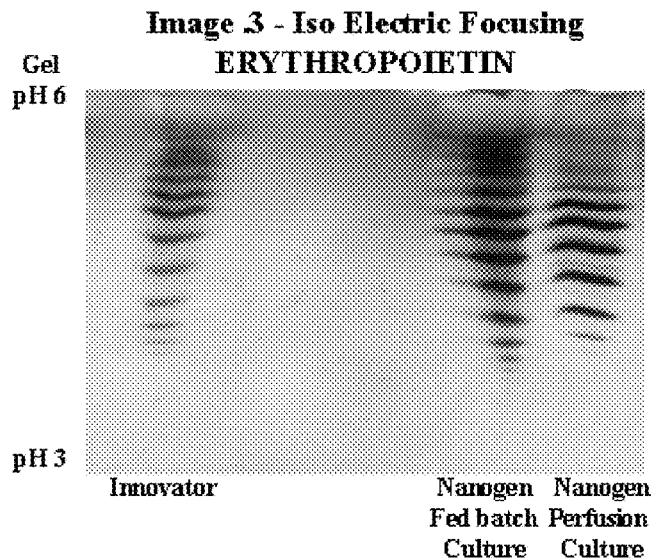

Fig. 19: Universal Medium Performance in Perfusion culture at 10L scale

Image .3 - Iso Electric Focusing
ERYTHROPOIETIN

Gel pH 6 pH 3

Innovator     Nanogen      Nanogen
              Fed batch    Perfusion
              Culture      Culture

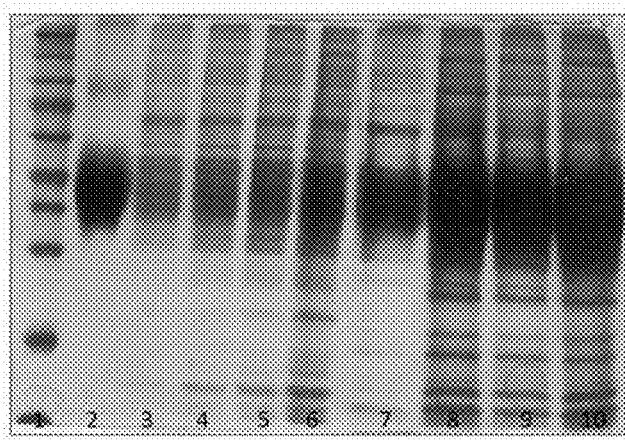

Fig. 20: Universal Medium Performance in Perfusion culture at 10L scale

Image. 4-12 % SDS-PAGE Reducing Gel

1. Protein Ladder
2. Innovator EPO
3. Harvest-1
4. Harvest-2
5. Harvest-3
6. Harvest-4
7. Harvest-5
8. Harvest-6
9. Harvest-7
10. Harvest-8

UNIVERSAL, GLYCOSYLATION ENHANCER, COMPLETELY CHEMICALLY DEFINED MEDIUM FORMULATION

RELATED APPLICATION

This application claims the benefit of U.S. Provisional Application No. 62/288,139 filed on Jan. 28, 2016, the content of which is incorporated herein by reference.

FIELD OF THE INVENTION

In one embodiment, this application discloses compositions and methods for the culturing of recombinant sub lineage cell lines of parent CHO cells at a high cell density to equal or more than 20 million cells/mL in suspension batch culture, expressing recombinant proteins with improved level of glycosylation which is necessary for its functionality for therapeutic use.

BACKGROUND OF THE INVENTION

Recombinant therapeutic proteins are increasingly important to the pharmaceutical industry. They represent valuable treatments against life threatening disease as well as investment opportunity for many biopharmaceuticals. Total global spending on medicines is estimated to reach $1 trillion by 2017, surpassing the 2012 spending level of $205-$235 billion. Surprisingly, data suggests that this growing share among all medicines class are biologic, with biosimilars or non-original biologics, making up about 20% of global pharmaceuticals market. These recombinant therapeutic proteins are divided into many sub classes such as hormones, monoclonal antibodies, fusion proteins, antibody fragments, vaccines, etc. . . . In general, these class of therapeutic proteins are expressed in a mammalian cells in a medium which provides all nutritional requirement to help cell growth and expression of these recombinant proteins. In the past, many recombinant therapeutic proteins approved by the FDA are expressed in variety of cells such as, but are not limited to, Chinese Hamster Ovary (CHO), Human Embryonic Kidney 293 cells, NS0, etc. . . . CHO cells have been repeatedly approved by regulatory agencies to manufacture these recombinant proteins. CHO cells' ability to culture easily in suspension and to produce high titers of human-compatible therapeutic proteins make CHO cells a popular choice as a host cells to produce these proteins at large scale.

CHO cells were first isolated in 1957 and its genomic resources are presently available. Parental CHO cell line was not able to produce many recombinant proteins at high titer and thus, many CHO sub lineage cell lines such as CHO-K1, CHO-DUX B11, CHO-S and DG44 were developed to achieve high titer and protein quality by random cell-line mutagenesis, media optimization and clonal selection. CHO-K1, which was derived from parental CHO cell line, contains a slightly lower amount of DNA than the parental CHO. CHO-K1 was mutagenized to generate CHO-DUX-B11 (also referred to as CHO-DUKX), a cell line lacking DHFR activity. These cells have a deletion of one DHFR allele and a missense mutation in the other. Subsequently, the Proline-dependent CHO-pro3-strain, another derivative of the original CHO cell line, was mutagenized to yield CHO-DG44, a cell line with deletions of both DHFR alleles.

It has also been reported that extensive mutagenesis and clonal selection of original CHO cells result in many missing genes in different CHO cell lines lineages, and detected >3.7 million single-nucleotide polymorphisms (SNPs), 551, 240 indels and 7,063 copy number variations. Many mutations are located in genes with functions relevant to bioprocessing, such as apoptosis. The details of this genetic diversity highlight that these cell lines are having different nutritional and metabolic requirements, different growth characteristics patterns and different ability to produce correctly folded and glycosylated protein in-vitro. Therefore, growth of these cells, expression and quality of recombinant proteins expressed in these cells depend on the culture medium composition and process conditions in which cells are expanded and maintained during the production phase of these proteins. This has been a challenge to scientists as they need either to develop the specific medium for their product expressed in these CHO sub lineage cells or screen out the wide range of commercially available mediums which is a time consuming and labor intensive task. Nutritional and metabolic requirements of cells in a transfected pool cells during clone development may also be different due to functionally heterogeneous or clonal variations. Apart from the different nutritional requirement for cell growth, the quality of expressed protein also depends on culture medium composition and conditions. Many therapeutic biologics products require glycosylation for their functionality which helps to increase the pharmacokinetics property and the half-life of recombinant therapeutic protein in the blood. Glycoproteins expressed in these CHO cells exhibits variation in glycan profile and sialylation. In general, glycosylation is an enzymatic site directed, post translational process occurs mainly in Endoplasmic reticulum organelle of a cell. In particular, a glycan composition sugar is transferred enzymatically and attached via a glycosidic bond in both branch or unbranch manner to the proteins, lipids or other molecules. pH stability of culture medium at large bioreactor scale may affect the glycosylation level of expressed recombinant protein in CHO cells. Thus, a successful mammalian manufacturing cell culture process depends on sufficient expression, glycosylation and correctly folded recombinant product which in turn largely depends on culture medium composition and its process conditions. The development of cell culture media formulations and their compositions have been well documented in literature, and a number of media are commercially available. Consequently, a great variety of different cell culture media have been developed. In early cell culture work, developed general chemical mediums largely depends on serum to provide cells nutritional requirements. Since serum has a significant number of disadvantages in manufacturing of bio therapeutics recombinant proteins such as undefined compositions, being the source of many pathogen, variability between batches, labor intensive purification process and its high cost. Therefore, serum became an unfavorable choice to scientists. A number of culture media offer serum replacement formulation. These media also suggest adding animal or plant extracts. However, the use of animal protein supplements in cell culture media also has certain drawbacks. For example, there is a risk that the culture medium and/or products purified from it may be immunogenic, particularly if the supplements are derived from an animal different from the source of the cells to be cultured. If biological substances intended to be used as therapeutics are purified from such culture media, certain amounts of these immunogenic proteins or peptides may be co-purified and may induce an immunological reaction, up to and including anaphylaxis, in an animal receiving such therapeutics.

Presently, there is a focus on the development of chemically defined media which ideally are deprived of serum, serum proteins, plant or animal proteins, plant or animal tissue/organ extract, lipids, steroids, antibiotic and soy hydrolysates. Different types of medium have been attempted such as serum free, protein free or chemical defined medium with a general focus to supplement the nutrients to a wide variety of cells for cells growth and expression of recombinant proteins. These media may be optimized to obtain a desired recombinant clone (CHO cell's sub lineage cell lines) by either supplementing with specific components or developing a feeding compositions. Further, many proteins such as insulin, transferrin, growth factors or animal/plant hydrolysates or other components may be added to optimize the cell growth of interest of clone. These suggested formulations seek to improve the cell growth and productivity in general. Specific aspects such as particular trace ions, carbohydrates or the content of specific amino acids in combination with additional features, replacement of insulin or transferrin, phospholipid precursors, and Na+/K+ ion channel have also been suggested.

Thus, it is clear that due to diversity of cell lines, production processes in use, the large number of media components involved, and the fact that many of those components are interdependent on each others because of the complexity of cellular metabolic pathways, media requirements for two different processes may differ greatly even when all other aspects of those processes are very similar. Even cell lines derived from a common parent often exhibit different nutritional requirements. For medium manufacturers, the requirements become even more diverse by the number of different cell line varieties and processes in common use today. For example, we wouldn't expect a medium designed for the batch culture of CHO cells to be the best medium for a fed-batch culture of mouse myeloma (NS0) cells. The nutritional requirements of those different cell lines and sub lineage cell lines are dissimilar, as are the requirements of different processes (batch and fed-batch).

Accordingly, there remains a need for a chemically defined, serum-free, protein-free, lipid-free, steroid-free, animal component-free and plant component-free, universal production medium which facilitates the growth of all sub lineage cell lines of CHO cells to high density, increases the level of glycosylation and production of correctly folded recombinant protein without the need of further medium optimization and adaptation.

BRIEF SUMMARY OF THE INVENTION

In one embodiment of the present application, there is provided a cell culture medium for culturing cell lines suitable for producing a therapeutic protein, comprising:

a) an amino acid selected from a group consisting of L-Arginine, L-Asparagine, L-Proline, Leucine and Hydroxyproline, or a mixture thereof;

b) a vitamin selected from a group consisting of ascorbic acid $Mg^{2+}$ salt, biotin, pyridoxine HCL, folic acid, riboflavin and D-calcium pantothenate, or a mixture thereof;

c) an element selected from a group consisting of ammonium meta vanadate, sodium meta vanadate, germanium dioxide, barium acetate, aluminum chloride, rubidium chloride, cadmium chloride, ammonium molybedate, stannous chloride, cobalt chloride, chromium sulfate, silver nitrate, sodium metasilicate, zinc sulfate, manganese sulfate $H_2O$, manganous chloride, ferric nitrate $9H_2O$, ferrous sulfate $7H_2O$, ferric ammonium citrate, magnesium chloride anhydrous, and magnesium sulfate anhydrous, or a mixture thereof;

d) a nucleoside selected from a group consisting of uridine and cystidine, or a mixture thereof;

e) a sugar selected from a group consisting of galactose, mannose and N-Acetyl-D-Mannosamine, or a mixture thereof; and f) a triple buffering system comprising sodium carbonate, sodium bicarbonate and HEPES; wherein the cell culture medium is animal component-free, plant component-free, serum-free, growth factors-free, recombinant protein-free, lipid-free, steroid-free, and free of plant or animal hydrolysates and/or extracts.

The disclosed medium may be used for culturing mammalian cell lines to produce recombinant therapeutic proteins. In one embodiment, the mammalian cell lines comprise CHO cell lines. In another embodiment, the CHO cell lines comprise CHO sub lineage cell lines such as CHO-K1, CHO-DUX B11, CHO-S and DG44 cell lines. In one embodiment, the CHO cell lines are capable of expressing wide variety of recombinant therapeutic class proteins.

The present application also discloses a method of using the universal production medium with naturally occurring chemicals at defined concentration in defined level to grow recombinant mammalian CHO sub lineage cells at high cell density equal to or more than 20 million cells/mL.

In one embodiment, the CHO cell lines may be grow in batch mode, fed-batch mode, continuous and perfusion culture without the need of medium optimization or adaptation for rapid production of therapeutic drugs. Further, the universal CHO cells medium may be enriched with one or more glycosylation enhancer components. In one embodiment, the medium completely lacks growth factors, proteins, lipids, hydrolysates, animals/plant's tissue/organ extracts and serums. The medium may preferably be used as production medium for commercial manufacturing of wide variety of glycosylated recombinant therapeutic proteins such as fusion proteins, hormones, mono clonal antibodies expressed in any sub lineage cells of CHO cell line.

The following embodiments, aspects and variations thereof are exemplary and illustrative are not intended to be limiting in scope. In addition to the exemplary embodiments, aspects and variations described above, further embodiments, aspects and variations will become apparent by reference to the drawings and figures and by examination of the following descriptions.

The foregoing examples of the related art and limitations are intended to be illustrative and not exclusive. Other limitations of the related art will become apparent to those of skill in the art upon a reading of the specification and a study of the drawings or figures as provided herein.

BRIEF DESCRIPTION OF THE DRAWINGS

FIG. 1 describes the comparability of universal production medium performance (Cell Growth as Indicator) with commercially available medium using recombinant CHO-DUX-B11-Darbepoetin cells at shake flask scale in a batch mode culture.

FIG. 2 describes the comparability of universal production medium performance (Cell Growth as Indicator) with commercially available medium using recombinant CHO-DG44-Erythropoietin cells at shake flask scale in a batch mode culture.

FIG. 3 describes the comparability of universal production medium performance (Cell Growth as Indicator) with commercially available medium using recombinant CHO-S-Etanercept cells at shake flask scale in a batch mode culture.

FIG. 4 describes the comparability of universal production medium performance (Cell Growth as Indicator) with commercially available medium using recombinant CHO-K1-Trastuzumab cells at shake flask scale in a batch mode culture.

FIG. 5 describes the high cell density growth profile of four recombinant CHO lineage cells in universal production medium at a 50 L single use shaken Bioreactor in a batch mode culture.

FIG. 6 describes the viability profile of four recombinant CHO lineage cells in universal production medium at a 50 L single use shaken Bioreactor in a batch mode culture.

FIG. 7 describes the combinatory effects of medium components on glycosylation of recombinant Erythropoietin expressed in CHO-DG44 cell line at shake flask scale.

FIG. 8 describes the effects of triple buffer system on glycosylation of recombinant Erythropoietin expressed in CHO-DG44 cell line at shake flask scale.

FIG. 9 describes the % recovery profile of recombinant CHO-DG44-Erythropoietin cells in universal production medium at shake flask in fed-batch culture.

FIG. 10 describes the % recovery profile of recombinant CHO-DUX-B11-Darbepoetin in universal production medium at shake flask in fed-batch culture.

FIG. 11 describes the high cell density growth and viability profile of recombinant CHO-DUX-B11-Darbepoetin and recombinant CHO-DG44-Erythropoietin cells in universal production medium at a 50 L single use shaken Bioreactor in fed-batch culture.

FIG. 12 describes the Osmolality profile of recombinant CHO-DUX-B11-Darbepoetin and recombinant CHO-DG44-Erythropoietin cells in universal production medium at a 50 L single use shaken Bioreactor in fed-batch culture.

FIG. 13 describes the Glucose profile of recombinant CHO-DUX-B11-Darbepoetin and recombinant CHO-DG44-Erythropoietin cells in universal production medium at a 50 L single use shaken Bioreactor in fed-batch culture.

FIG. 14 describes the pH profile of recombinant CHO-DUX-B11-Darbepoetin and recombinant CHO-DG44-Erythropoietin cells at a 50 L single use shaken Bioreactor in fed-batch culture.

FIG. 15 describes % recovery after purification of recombinant CHO-DUX-B11-Darbepoetin and recombinant CHO-DG44-Erythropoietin cells at a 50 L single use shaken Bioreactor in fed-batch culture.

FIG. 16 describes the high productivity profile of recombinant CHO-S-Etanercept cells in universal production medium at a 50 L single use shaken Bioreactor in fed-batch culture.

FIG. 17 describes performance of the universal medium in fed batch culture at 50 L scale.

FIG. 18 describes performance of the universal medium in fed batch culture at 50 L scale.

FIG. 19 describes performance of the universal medium in perfusion culture at 10 L scale FIG. 20 describes performance of the universal medium in perfusion culture at 10 L scale.

DETAILED DESCRIPTION OF THE INVENTION

Definitions

The term "amino acid" as used herein refers to amino acids, such as, for example, L-alanine, L-arginine, L-asparagine, L-asparaginic acid, L-glutamine, L-glutamic acid, glycine, L-histidine, L-isoleucine, L-leucine, L-lysine, L-methionine, L-ornithine, L-phenylalanine, L-proline, L-threonine, L-triptophane, and L-valine, preferably, L-alanine, L-arginine, L-asparagine, L-asparaginic acid, L-glutamine, L-glutamic acid, glycine, L-histidine, L-isoleucine, L-leucine, L-lysine, L-methionine, L-phenylalanine, L-proline, L-threonine, L-triptophane and L-valine.

The term "buffering system" as used herein refers a system or agent(s) that has a buffering range suitable for maintaining a pH range suitable for culturing mammalian cell lines such as CHO cell lines suitable for expressing therapeutic proteins. Example of a buffering system agent may include a triple buffering system comprising sodium carbonate, sodium bicarbonate and HEPES. Other system or agent may include MOPS, TES (2-[tris (hydroxymethyl) methyl]amino ethanesulphonic acid and imidazole.

A "chemically defined cell culture medium" or "CDM" is a medium with a specified composition that is free of animal-derived products such as animal serum and peptone. The terms also encompass a medium with a specified composition that is free of undefined or partially defined components, for example, components such as an animal serum, an animal peptone, and a plant peptone. As would be understood by a person of skill in the art, a CDM may be used in a process of polypeptide production whereby a cell is in contact with, and secretes a polypeptide into, the CDM. Thus, it is understood that a culture may contain a CDM and a polypeptide product and that the presence of the polypeptide product does not render the CDM chemically undefined.

The term "CHO cells", "CHO cell lines" or "CHO sub lineage cells" or "CHO cell lines" as used herein refer to Chinese hamster ovary cell lines. CHO cell lines may include CHOK1, CHO DUX-B11, CHO DG44 and other CHO cell lines.

The term "cell culture medium" or "medium" or "production medium" as used herein may be used interchangeably and refers to a mixture or source of nutrients/ingredients to grow cells which are suitable for the production of therapeutic proteins. The medium may be dry or aqueous. The dry medium may be reconstituted into an aqueous medium. As is understood by a person of skill in the art, the nutrient source may contain components required by the cell for growth and/or survival or may contain components that aid in cell growth and/or survival. Vitamins, nucleosides, sugars, essential or non-essential amino acids, trace amount of elements, etc. . . . are examples of medium components.

The term "fed-batch" as used herein refers to a method of supplying the composition of the cell culture medium of the present application to cells such that the concentration of a reagent is additive of the individual additions of the reagent. Cell culture may be classified into batch culture, continuous culture and fed-batch culture. The batch culture is a process that allows cells to grow by addition of a small amount of a seed culture solution to the culture medium, without addition of a fresh medium during culturing or without discharge of the culture medium used for the culture. The continuous culture is a culturing process that involves continuous addition of a fresh medium and continuous discharge of the medium used for the culture. The fed-batch culture is a culturing process that involves continuous or consecutive addition of a fresh medium with or without periodic cell and/or product harvest before termination of culture. The culture medium to be added during the fed-batch culture (also referred to as fed-batch medium) is not necessarily the same as that of the culture medium that has been used for the initial culture medium. Therefore, a different medium or only a specific component may be fed.

The term "mammalian cell culture medium" as used herein refers to a mixture of components which maintain and/or support the in vitro growth of mammalian cells. Examples of mammalian cells are human or animal cells, such as CHO cells, COS cells, I VERO cells, BHK cells, AK-1 cells, SP2/0 cells, L5.1 cells, hybridoma cells or human cells.

The term "perfusion culture" as used herein refers to a culture by which the cells are restrained in the culture by, e.g., filtration, encapsulation, anchoring to microcarriers, etc. . . , and the culture medium is continuously or intermittently introduced and removed from the culturing vessel.

The term "nucleoside" as used herein refers nucleoside such as deoxyadenosine, deoxycytidine, deoxyguanosine, adenosine, cytidine, guanosine or uridine.

The terms "polypeptide" and "protein" are used interchangeably herein to refer to polymers of amino acids of any length, including the therapeutic proteins as disclosed herein. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Examples of polypeptides encompassed within the definition herein include mammalian proteins, such as, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to a protein, including, for example, any of the above-listed proteins.

The term "serum-free" and "protein-free medium" as used herein refer to a fully chemically defined medium which contains no additives from animal source like tissue hydrolysates, e.g. fetal bovine serum or the like.

The term "therapeutic proteins" or "recombinant protein" or "therapeutically active recombinant proteins" as used herein may be used interchangeably and referred to proteins that are engineered in the laboratory for pharmaceutical use. Due to recombinant DNA-technology proteins can be generated in specific host cells (e. g. bacteria, yeast or mammalian cells) under defined conditions. The production host may be chosen depending on the requirements of the protein. Mammalian cells may be the main host of choice because their post translational modifications such as glycosylation and sialylation have the biggest impact on the protein's pharmacokinetics and efficiency. Therapeutic proteins are used for example in the treatment of cancer, infectious diseases, hemophilia, anemia, multiple sclerosis and hepatitis B/C. Therapeutic proteins can also be grouped based on their molecular types that include antibody-based drugs, Fc fusion proteins, anticoagulants, blood factors, bone morphogenetic proteins, engineered protein scaffolds, enzymes, growth factors, hormones, interferons, interleukins, and thrombolytics.

The term "titer" as used herein refers to the total amount of recombinantly expressed proteins produced by a cell culture divided by a given amount of medium volume. Titer may be expressed in units of milligrams of polypeptide per milliliter of medium.

The term "trace amount" or "trace quantity" as used herein refers to the amount of an element that is added to cell culture medium in very minute quantities for the proper growth of cell lines. For example, the following elements, such as metal elements, calcium, magnesium, molybdenum, cobalt, copper, manganese, zinc, selenium, iron and combinations thereof may be added in trace amount to the medium. Other elements may be added in trace amounts include copper sulfate, manganese sulfate, zinc sulfate, magnesium sulfate, nickel chloride, tin chloride, magnesium chloride, and/or sodium silicite. Other elements that may be added include transitional metal elements. Other elements may also be added in trace amount include ammonium meta vanadate, sodium meta vanadate, germanium dioxide, barium acetate, aluminum chloride, rubidium chloride, cadmium chloride, ammonium molybedate, stannous chloride, cobalt chloride, chromium sulfate, silver nitrate, sodium metasilicate, zinc sulfate, manganese sulfate $H_2O$, manganous chloride, ferric nitrate $9H_2O$, ferrous sulfate $7H_2O$, ferric ammonium citrate, magnesium chloride anhydrous, and magnesium sulfate anhydrous, or a mixture thereof.

The term "vitamin" as used herein may include, but is not limited to, i-inositol, ascorbic acid, biotin, flavin adenine dinucleotide, folic acid, folinic acid, lipoic acid, nicotinamide, nicotinic acid, p-amino-benzoic acid, pantothenate, pyridoxal hydrochloride, pyridoxine, riboflavin, thiamine, vitamin B12 and combinations thereof.

The term "universal production medium" as used herein refers to a mixture of nutrients for growing cells at high cell density over a prolonged period of time. Production media may include the following components: A source of energy, usually a carbohydrate compound such as glucose, amino acids such as all essential amino acids, vitamins and/or other organic compounds at concentrations suitable for culturing cells, free fatty acids, and inorganic compounds including elements at trace amount, inorganic salts, buffering compounds, nucleosides and bases. The ingredients or components of a cell culture medium or production medium may be added in any combination thereof.

In one aspect of the present application, there is provided a cell culture medium for culturing cell lines suitable for producing a therapeutic protein, comprising:
a) an amino acid selected from a group consisting of L-Arginine, L-Asparagine, L-Proline, L Leucine and L Hydroxyproline, or a mixture thereof;
b) a vitamin selected from a group consisting of ascorbic acid $Mg^{2+}$ salt, biotin, pyridoxine HCL, folic acid, riboflavin and D-calcium pantothenate, or a mixture thereof;
c) an element selected from a group consisting of ammonium meta vanadate, sodium meta vanadate, germanium dioxide, barium acetate, aluminum chloride, rubidium chloride, cadmium chloride, ammonium molybedate, stannous chloride, cobalt chloride, chromium sulfate, silver nitrate, sodium metasilicate, zinc sulfate, manganese sulfate $H_2O$, manganous chloride, ferric nitrate $9H_2O$, ferrous sulfate $7H_2O$, ferric ammonium citrate, magnesium chloride anhydrous, and magnesium sulfate anhydrous, or a mixture thereof;
d) a nucleoside selected from a group consisting of uridine and cystidine, or a mixture thereof;
e) a sugar selected from a group consisting of galactose, mannose and N-Acetyl-D-Mannosamine, or a mixture thereof; and
f) a triple buffering system comprising sodium carbonate, sodium bicarbonate and HEPES; wherein the cell culture medium is animal component-free, plant component-free, serum-free, growth factors-free, recombinant protein-free, lipid-free, steroid-free, and free of plant or animal hydrolysates and/or extracts.

In one embodiment, wherein the cell culture medium comprises: about 350 to about 500 mg/L L-arginine; about 700 to about 900 mg/L L-asparagine; about 350 to about 500 mg/L L-proline; about 500 to about 650 mg/L leucine; and about 90 to about 110 mg/L hydroxyproline.

In another embodiment, the cell culture medium comprises: about 8 to about 14 mg/L ascorbic acid $Mg^{2+}$ salt; about 1.0 to about 1.5 mg/L biotin; about 2.5 to about 4 mg/L pyridoxine HCL; about 19 to about 23 mg/L folic acid; about 0.4 to about 0.6 mg/L riboflavin; and about 3 to about 4 mg/L D-calcium pantothenate.

In another embodiment, the cell culture medium comprises: about 1 to about 1.5 µg/L ammonium meta vanadate; about 1 to about 1.8 µg/L sodium meta vanadate; about 0.2 to about 0.8 µg/L germanium dioxide; about 2 to about 3 µg/L barium acetate; about 1 to about 1.6 µg/L aluminum chloride; about 1.1 to about 1.7 µg/L rubidium chloride; about 35 to about 75 µg/L cadmium chloride; about 5 to about 20 µg/L ammonium molybedate; about 0.1 to about 0.5 µg/L stannous chloride; about 5 to about 15 µg/L cobalt chloride; about 0.1 to about 1 µg/L chromium sulfate; about 0.1 to about 0.2 µg/L silver nitrate; about 200 to about 600 µg/L sodium metasilicate; and about 100 to about 600 µg/L zinc sulfate.

In one embodiment, the cell culture medium comprises about 15 to about 25 mg/L uridine and about 18 to about 25 mg/L cytidine.

In another embodiment, the cell culture medium comprises: about 0.1 to about 0.9 mg/L manganese sulfate $H_2O$; about 0.1 to about 0.5 mg/L manganous chloride; about 0.3 to about 2 mg/L ferric nitrate $9H_2O$; about 2 to about 5 mg/L ferrous sulfate $7H_2O$; about 1 to about 2.5 mg/L ferric ammonium citrate; about 40 to about 100 mg/L magnesium chloride anhydrous; and about 10 to about 20 mg/L magnesium sulfate anhydrous. In one embodiment, the cell culture medium comprises: about 100 mg to about 500 mg/L galactose; about 100 to about 500 mg/L mannose; about 50 to about 150 mg/L N-acetyl-D-mannosamine; and about 100 to 300 mg/L glucosamine. In various embodiments, the cell culture medium comprises the triple buffering system comprising: about 1.5 g/L sodium carbonate; about 2.2 g/L sodium bi carbonate; and about 2.38 g/L HEPES.

In various embodiments disclosed herein, the cell culture medium is capable of growing the cell lines at a cell density of more than 20 million cells/mL. In one embodiment, the cell culture medium may be used to grow the cell lines in a batch mode culture without the need of cell clone adaptation.

In one embodiment, the cell culture medium enhances glycosylation of therapeutic protein by about 20% to about 200%. In another embodiment, the cell culture medium enhances glycosylation of therapeutic protein by about 20%, 30%, 40%, 50%, 60%, 70%, 80%, 100%, 120%, 130%, 140%, 150%, 160%, 170%, 180%, 190% and 200%.

In various embodiments, the cell culture medium may increase the expression of recombinant proteins in a fed-batch mode culture by about 5%, 10%, 20%, 30%, 40%, 50%, 60%, 70%, 80%, 90%, 100%, 120%, 130%, 140%, 150%, 160%, 170%, 180%, 190% and 200%.

In other embodiments, the cell culture medium may increase the expression of recombinant proteins in a batch mode culture by about 5%, 10%, 20%, 30%, 40%, 50%, 60%, 70%, 80%, 90%, 100%, 120%, 130%, 140%, 150%, 160%, 170%, 180%, 190% and 200%.

In one aspect of the present application, the cell culture medium is useful in commercial manufacturing of therapeutic proteins. In one embodiment, the cell culture media disclosed in the present application display surprising and unexpected advantage over presently available cell culture media.

In yet another embodiment, the cell culture media disclosed in the present application provides surprising results and unexpected advantage in manufacturing therapeutic protein such as hormones, monoclonal antibodies and enzymes.

In one aspect of the present application, the cell culture medium is useful in culturing cell lines, including CHO cell lines. In various embodiments, the CHO cell lines comprise CHO DUX B11, CHO K1, CHO DG44, CHO-M and CHO-S cell lines.

In one aspect of the present application, there is provided a method of culturing cell lines suitable for producing a therapeutic protein, comprising contacting the cell lines as disclosed herein with a cell culture medium according to various embodiments contained in the present application.

In one aspect, there is provided a kit for culturing CHO cell lines suitable for producing a therapeutic protein, comprising a cell culture medium with the composition as disclosed in various embodiments herein The present application also provide a method for culturing of all CHO cell lines including sub lineage cell lines thereof at a high cell density of equal to or more than 20 million cells/mL. In one embodiment, the cell lines may be cultured without the need of medium optimization and adaptation.

In yet another aspect, mammalian cell lines, including CHO cell lines/sub lineage cell lines may be cultured in suspension batch culture, in a cell culture medium as disclosed in the present application.

Further, the cell culture medium and method of culturing cell lines disclosed herein provide for enhanced expression of recombinant proteins with improved glycosylation. In one embodiment, the medium disclosed herein may be enriched with elevated level of one of more amino acids.

In one embodiment, the medium may be enriched with 350-500 mg/L L-arginine, 700-900 mg/L L-asparagine, 350-500 mg/L L-proline, 500-650 mg/L leucine and 90-110 mg/L hydroxyproline.

In another embodiment, the medium may be enriched with elevated level of one or more vitamins. In one embodiment, the medium may be enriched with 10-12 mg/L ascorbic acid $Mg^{2+}$ salt, 1.0-1.2 mg/L biotin, 2.5 to 4 mg/L pyridoxine HCL, 19-23 mg/L folic acid, 4-6 mg/L riboflavin and D-calcium pantothenate.

In yet another embodiment, the medium may be enriched with elevated level of one or more elements. In one embodiment, the medium may be enriched with a trace amount of one or more elements. In another embodiment, the medium may be enriched with about 1.25 to 1.50 μg/L ammonium meta vanadate, 1.10 to 1.40 μg/L sodium meta vanadate, 0.4 to 0.6 μg/L germanium dioxide, 2.4 to 2.8 μg/L barium acetate, 1.1 to 1.40 μg/L aluminum chloride, 1.25 to 1.50 μg/L rubidium chloride, 42 to 50 μg/L cadmium chloride, 10 to 14 μg/L ammonium molybedate, 0.1 to 0.3 μg/L stannous chloride, 8-11 μg/L cobalt chloride, 0.5 to 0.7 μg/L chromium sulfate, 0.16 to 0.20 μg/L silver nitrate, 300 to 450 μg/L sodium metasilicate and 300 to 500 μg/L zinc Sulfate.

In one aspect of the present application, the medium is surprisingly found to increase the overall glycosylation of recombinant proteins with the addition of nucleosides. In one embodiment, 18 to 22 mg/L uridine, 18 to 22 mg/L cytidine. Other nucleosides may also be used to enrich the medium. Particularly, nucleosides which are part of precursors of protein's glycosylation may be used to increase glycosylation of recombinant proteins.

In yet another aspect of the present application, the medium is surprisingly found to increase the overall glycosylation of recombinant proteins with the addition of trace amounts of one or more elements. In one embodiment, the following trace amounts were added to the medium: 0.25 to 0.5 mg/L manganese sulfate $H_2O$; 0.15 to 0.30 mg/L manganous chloride; 1.1 to 1.3 mg/L ferric nitrate $9H_2O$; 3.0 to 4.0 mg/L ferrous sulfate $7H_2O$; 1.4 to 1.7 mg/L ferric ammonium citrate; 60 to 80 mg/L magnesium chloride anhydrous; and 12 to 18 mg/L magnesium sulfate anhydrous.

In one aspect, the addition of trace amounts of one or more elements appears to support the function of many glycosyltransferases enzymes to increase the glycosylation. In yet another aspect, one or more sugars may be used to enrich the medium. In one embodiment, the medium may be enriched with 200 mg to 300 mg/L galactose, 200 to 300 mg/L mannose, 80 to 100 mg/L N-acetyl-D-mannosamine and 200 to 250 mg/L glucosamine. In one embodiment, one or more sugars which are part of many protein's glycan structure may be added to the medium to increase the glycosylation of recombinant therapeutic proteins.

In yet another aspect, it is surprisingly found that the overall glycosylation of recombinant proteins may be enhanced by the use of triple buffering system. In one embodiment, the triple buffering system comprises 1.5 g/L sodium carbonate, 2.2 g/L sodium bicarbonate and 2.38 g/L HEPES for stabilization of pH fluctuation in the culture environment to control for the osmolality of culture medium and to facilitate improved glycosylation of recombinant proteins.

In one aspect of the present application, the medium is directed to culturing mammalian cell lines. In one embodiment, the mammalian cell lines comprise CHO cell lines. In another embodiment, the CHO cell lines comprise CHO sub lineage cell lines such as CHO-S, CHOK1, CHO DUXB11, CHO-M and CHO-DG44 cell lines.

In another aspect, the medium disclosed herein may be defined to be CHO cell line specific production medium for the production of glycosylated recombinant proteins using such cell lines.

In one aspect, the present application is directed to the use a universal cell culture medium. In one embodiment, the cell culture medium comprises a completely chemically defined medium and free of serum, peptides, lipids, steroids, antibiotic, animal components, plant components.

In one embodiment, the medium comprises elevated levels of one or more amino acids. In one embodiment, the amino acid comprises essential and non-essential amino acids. In another embodiment, the amino acid comprises L-arginine, L-asparagine, L-proline, L leucine and L hydroxyproline.

In one embodiment, the medium comprises vitamins. In another embodiment, the medium comprises glycosylation enhancer elements in trace amount. In one embodiment, the enhancer elements comprises $Mn^{2+}$, $Mg^{2+}$ and $Fe^{2+}$. In one aspect of the present application, the invention may be used to eliminate the requirement to develop clone specific medium for CHO cells, and to improve the glycosylation of recombinant proteins. The disclosed invention may be used for production of glycosylated recombinant therapeutic proteins at commercial scale.

Generally, use of material of biological origin is not allowed in production media for the production of therapeutically active recombinant proteins due to safety and contamination issues. Therefore, the production medium according to the present application is preferably a serum-free, protein-free, lipids free, animal/plant component free medium.

In one embodiment, proteins, especially growth factors like insulin, transferrin or the like are preferably not added to the cell culture medium disclosed herein. In another embodiment, the universal production medium disclosed herein is also not supplemented with a hydrolysed protein source like soybean, wheat or rice peptone or yeast hydrolysate or the like. Further, lipids like cholesterol, steric acid, palmitic acids etc., are also not added to the medium. In another embodiment, steroids such as hydrocortisone or its derivatives, nucleosides like hypoxanthine or its derivatives, antibiotic like gentamicin, streptomycin or any other, and phenol red are also not added to the medium.

In one embodiment, the osmolality and pH of the media are adjusted to values that allow for the growth of the cells. In one embodiment, pH ranges from about 6.8 to about 7.2. The osmolality of the media at the beginning of culturing may be between about 260 and about 300 mOsm.

In one embodiment, the cells may be initially grown at temperatures of about 36° C. to about 37° C. In another embodiment, the temperatures may be adjusted by one skilled in the art to optimize CHO cells growth. In one aspect, one or more amino acids select from the group consisting of 20 essential amino acids may be added at elevated level to the medium. In one embodiment, L-arginine, L-asparagine, proline, leucine and L hydroxyproline may be added to the medium.

Various compositions of the cell culture medium may be found in Table 1-6. One aspect of the present application is related to increasing the glycosylation of expressed protein using host cells of any one of the CHO cell lines and sub cell lines cultured in the production medium. Many therapeutic biologics products require glycosylation for their functionality, increasing the pharmacokinetics property and the half life of recombinant therapeutic protein in the blood. Glycoproteins expressed in CHO cells exhibits variation in glycan profile and sialylation. In general, glycosylation is an enzymatic site directed, post translational process occurs mainly in endoplasmic reticulum organelle of a cell. In particular, a glycan composition sugar is transferred enzymatically and attached via a glycosidic bond in both branch or unbranch manner to the proteins, lipids or other molecules.

Additional components of the medium disclosed herein may be found in Table 5. In one embodiment, co-factors for enzymes, such as but not limited to, glycosyltransferase and glycan processing enzymes involved in making backbone of glycan composition of a protein in endoplasmic reticulum may be added to the medium.

In another embodiment, glycan backbone composition's sugars to ensure the availability of these sugars during expression of recombinant proteins may be added to the medium, and supplemented with those nucleosides involved in nucleotide sugar donor group transfer reaction during glycan processing in endoplasmic reticulum.

In one variation, a triple buffering system of sodium carbonate, sodium bicarbonate and HEPES may be used to maintain the desirable pH range of the medium. In another embodiment, the present medium and method of culturing the CHO cell lines increases the productivity of recombinant proteins significantly in a fed-batch or a perfusion culture. In yet another embodiment, the medium is useful for producing a recombinant protein in vitro with increased glycosylation of those recombinant therapeutic proteins which require glycosylation for its functionality in human beings.

In one aspect, the medium disclosed herein reduces the immunological side effects which may arise from using medium which is not serum free, protein free, animal/plant component at commercial manufacturing scale. Further, use of the present medium may meet regulatory requirements to expedite the process for getting market authorization approval for therapeutic protein.

In one aspect, the method disclosed herein for producing a protein comprises culturing mammalian cell lines such as CHO cell lines that express the protein at a temperature below 37° C., optionally from about 29° C. to about 36° C. or from about 29° C. to about 35° C. or from about 30° C. to about 33° C.

In another aspect, there is provided a culture medium comprising N-acetyl D-mannosamine, galactose, glucosamine, fructose and mannose. In one embodiment, the concentration of N-acetyl D-mannosamine may be at least about 0.8 millimolar (mM), optionally at least about 2 mM, at least about 3 mM, at least about 4 mM, at least about 5 mM, at least about 10 mM, or at least about 20 mM, and the concentration of galactose can be from about 1 mM to about 5 mM, optionally from about 2 mM to about 4 mM, or from about 2.5 mM to about 3.5 mM. The concentrations of fructose and mannose, when present, can be the same as or different from those of each other and those of galactose and N-acetyl D-mannosamine. The concentrations of fructose and mannose can be from about 1 mM to about 5 mM each, optionally from about 2 mM to about 4 mM each, or from about 2.5 mM to about 3.5 mM each.

In various aspects of the present application, suitable cells for applying the present medium include any cell line that can glycosylate proteins. In one embodiment, a mammalian cell line may be used. In another embodiment, the cells are homogenous cell lines. Other cell lines may also be used, such as VERO, BHK, Cos, MDCK, 293, 3T3, myeloma (e.g. NSO, NSI), or WI38 cells. In another embodiment, hybridoma cell lines that produce an antibody can also be used with the medium disclosed herein. Cell lines derived from the above-mentioned cells are also suitable with the medium.

In one aspect, the medium can be enriched by the addition of a nutrient or component as disclosed hereinat greater than its usual, recommended concentration, for example at 2×, 3×, 4×, 5×, 6×, 7×, 8×, or even higher concentrations. As used herein, "1×" means the standard concentration or the standard concentration range as disclosed herein, "2×" means twice the standard concentration or concentration range, etc. . . .

In various embodiments, one or more vitamins as disclosed herein may be added to the medium at a concentration of from about 0.5 mg/L to about 50.0 mg/L; 1 mg/L to 45 mg/L; 1.5 mg/L to 40 mg/L; 2 mg/L to 35 mg/L; 3 mg/L to about 30 mg/L; 4 mg/L to 25 mg/L; 5 mg/L to about 20 mg/L; 7 mg/L to 15 mg/L; 10 mg/L to 12 mg/L.

In various embodiments, one or more vitamins may also be added at a concentration range of from about 0.05 mg/L to about 5.5 mg/L; from about 0.05 mg/L to about 5.0 mg/L; from about 0.05 mg/L to about 4.5 mg/L; from about 0.05 mg/L to about 4.0 mg/L; from about 0.05 mg/L to about 3.5 mg/L; from about 0.05 mg/L to about 3.0 mg/L; from about 0.05 mg/L to about 2.5 mg/L; from about 0.05 mg/L to about 2.0 mg/L; from about 0.05 mg/L to about 1.5 mg/L; from about 0.05 mg/L to about 1.0 mg/L; from about 1.0 mg/L to about 10.0 mg/L; from about 1.5 mg/L to about 10.0 mg/L; from about 2.0 mg/L to about 10.0 mg/L; from about 2.5 mg/L to about 10.0 mg/L.

In another aspect, one or more elements such as metal elements disclosed herein may be added to the medium at a range of from about 2 μM to about 80 μM; from about 2 μM to about 40 μM; from about 2 μM to about 30 μM; from about 2 μM to about 25 μM; from about 2 μM to about 20 μM; from about 2 μM to about 15 μM; from about 2 μM to about 10 μM; from about 10 μM to about 50 μM; from about 15 μM to about 50 μM; from about 20 μM to about 50 μM; from about 25 μM to about 50 μM; from about 30 μM to about 50 μM; from about 40 μM to about 50 μM; from about 10 μM to about 40 μM; from about 10 μM to about 30 μM; from about 10 μM to about 25 μM; from about 15 μM to about 25 μM; from about 15 μM to about 20 μM; about 5 or 10 or 15 or 20 or 25 or 30 or 35 or 40 μM. Elements which may be added in very small amount such as inorganic compounds disclosed herein may be added to the medium at very low final concentrations.

On yet another aspect, particular ions such as, but not limited to sodium, chloride, calcium, magnesium, and phosphate may be added to the medium. Other ions are also disclosed in this application, for example in Table 1-5.

In yet another aspect of the present application, cells may be cultured in a variety of vessels including, for example, perfusion bioreactors, cell bags, culture plates, flasks and other vessels well known to those of ordinary skill in the art. Ambient conditions suitable for cell culture, such as temperature and atmospheric composition, are also known in the art. Methods for the culture of cells are also well known to those skilled in the art.

In yet another aspect, the medium may be useful in the culture of eukaryotic cells. In various embodiments, the eukaryotic cells may have insect, avian, mammalian, or other origins. In one embodiment, the cells such as mammalian cells may be cultured in aqueous medium comprising the medium of the application. In another embodiment, the culture may be a suspension culture or an adherent culture. In yet another embodiment, cells may also be cultured by suspension in semi-solid medium comprising the medium of the application.

In one embodiment, the mammalian cells comprise myeloma derived cells, non-immortalized cells of the B cell lineage, and immortalized cells of the B cell lineage such as hybridomas. Those skilled in the art will recognize other myeloma cell lines and myeloma derived cell lines as well as any supplements required for the successful culture of such cells.

Individual media components may be present in amounts that result in one or more advantageous properties (such as one or more acceptable product quality attribute). In one variation, a cell culture medium as provided herein contains media components or combination or mixture thereof in amounts as described in Table 1-6. It is understood that a medium may comprise any one or more of the medium components of Tables 1-6 and in any combination/mixture that may be advantageous to growing cells.

In various embodiments, media components may be added to a composition in forms that are known in the art. For example, vitamin B2 may be provided as riboflavin powder, vitamin B6 may be provided as pyridoxine HCl or as pyridoxal HCl, vitamin B9 may be provided as folic acid powder, vitamin B 12 may be provided as cyanocobalamin powder, cysteine may be provided as L-cysteine monohydrochloride monohydrate powder, cystine may be provided as disodium salt monohydrate powder. In some embodiments, vitamin B6 is not provided as pyridoxal HCl. In an additional non-limiting example, vitamin B1 may be provided as thiamine monohydrochloride, vitamin B3 may be provided as niacinamide, vitamin B5 may be provided as D-calcium pantothenate, and vitamin B7 may be provided as biotin. As another non-limiting example, iron may be added in different iron forms or iron sources. In some embodiments, an iron source is ferric citrate or ferrous sulfate. Media components described herein can be provided in the form of a salt, a hydrate, a salt hydrate, or as a solution, an extract, or in solid form.

In various embodiments of the present invention, examples of vitamins may include Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Various embodiments may also comprise vitamin precursors.

In various embodiments, examples of salts comprise components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn.

In other embodiments of the present invention, examples of buffers comprise $CO_2/HCO_3$, HEPES, PIPES, ACES, BES, TES, MOPS and TRIS.

In other embodiments, the medium of the present invention may comprise nucleic acid components. In various embodiments, the nucleic acid component comprises nucleobases, for example, cytosine, guanine, adenine, thymine or uracil; nucleosides, for example, cytidine, uridine, adenosine, guanosine and thymidine; and nucleotides, for example, adenosine monophosphate or adenosine diphosphate or adenosine triphosphate.

In various embodiments disclosed herein, the cell culture medium may comprise one or more saccharide components, one or more amino acids, one or more vitamins, one or more salts or trace elements, one or more buffer components, one or more co-factors and one or more nucleic acid components. Saccharide components may comprise all mono- or di- or poly-saccharides. In various embodiments, saccharides may comprise glucose, galactose, ribose, fructose, sucrose, lactose, maltose, mannose, N-acetyl-D-Mannosamine, or glucosamine.

In other embodiments, amino acids may also comprise protein precursors. In some embodiments, amino acids may comprise leucine, isoleucine, lysine, methionine, phenylalanine, threonine, tryptophane, or valine. Amino acids may also comprise D-amino acids.

In various embodiments, the medium does not comprise peptones or tryptones.

It is understood that mammalian cells and therapeutic proteins may be cultured in the medium disclosed herein by batch culture, repeated batch culture, fed-batch culture, repeated fed-batch culture, continuous culture, or perfusion culture.

It is also understood that a person skilled in the art will know that concentration of the amino acids or peptides in the culture solution varies depending on types of cells and conditions for culture. For example, a concentration of the amino acids in the culture medium may be in the range of about 0.1 to about 100 mM, about 0.2 to about 50 mM, or about 0.5 to about 25 mM, as the final concentration in a culture solution.

In various embodiments, the medium may comprise peptide comprising 2 to 10 residues of amino acids. In various embodiments of the culture medium disclosed herein, the medium does not contain plasma proteins, hormones, and growth factors.

In other aspects of the present application, the cell culture medium may be used to manufacture recombinant antibody (e.g., a natural antibody, an antibody fragment, a low-molecular-weight antibody, a chimeric antibody, a humanized antibody, and a bispecific antibody); and a recombinant protein (e.g., granulocyte colony-stimulating factor (G-CSF), granulocyte-macrophage colony-stimulating factor (GM-CSF), erythropoietin, interferon, interleukin such as IL-1 or IL-6, t-PA, urokinase, serum albumin, and a blood coagulation factor).

In other aspects, antibody produced using the medium disclosed herein comprise monoclonal antibodies derived from animals such as human, mouse, rat, hamster, rabbit, and monkey, artificially modified recombinant antibodies such as chimeric antibodies, humanized antibodies, and bispecific antibodies. In yet other aspects, antibody may comprise immunoglobulin, e.g. any of IgG (such as IgG1, IgG2, IgG3, and IgG4), IgA, IgD, IgE, and IgM, for use as pharmaceutical drugs. In other aspects, the antibody of the present invention may be a whole antibody or a low-molecular-weight antibody such as an antibody fragment (e.g., Fv, Fab, or F(ab)$_2$) or a monovalent or divalent single-chain Fv (e.g., scFv or sc(Fv)$_2$).

PREPARATION AND EXAMPLES

The liquid medium of universal production medium was prepared by mixing of components in a specific sequence manner to ensure better dissolution of each component in the mixer. All the components were purchased and used from SIGMA fine chemicals. The water used in this application was endotoxin free purified sterile water. The sequence and methodology to prepare one liter of universal medium is described here below:
1. Prepare the 1000× stocks of all trace elements in water at neutral pH (Table 3);
2. Prepare a 100× of L-Tyrosine Disodium Salt in a high pH water (pH 9.0 to pH 10.0) (Table 1);
3. Prepare a 100× of Biotin, Folic, Riboflavin at a high pH water (pH 9.0 to pH 10.0) (Table 2);
4. Mix rest all the amino acids at low pH water (pH 0.8 to pH 1.0), stir for 30 minutes (Table 1);
5. Add the remaining Vitamins, 1× Trace elements, and Sodium bicarbonate and HEPES (From Step 1);
6. Add 1× concentration of L-Tyrosine Disodium Salt, Biotin, Folic, Riboflavin (From Steps 2, 3);
7. Add the remaining components except sodium chloride and mix for 2 hours at room temperature (Table 4);
8. Adjust the pH to 6.9 to 7.0 by using 5N NaOH, mix for 1 hours at room temperature;
9. Adjust the Osmolality to 280 to 300 mOsm using sodium chloride, mix for 2 hours at room temperature;
10. Sterile filtration by 0.2 micron membrane filtration.

Example 1

Culturing of recombinant CHO sub lineage cell lines in universal production medium in batch mode culture at shake flask scale and comparing its performance with commercially available medium.

Four CHO sub lineage cells, e.g. CHOK1, CHO-S, CHO DUX-B11, and CHO DG44, (obtained from ATCC/OTHERS) were selected and transfected with cDNA encoding of four different class of therapeutic proteins in 96 well plate. The combination of cells and cDNA used to transfect is shown in Table-7. A standard process for generation of stable clone was used for all cell lines. The selection of transfected cells was done using the DHFR selection marker. After selection of transfected cell pool, a stable pool was formed by increasing the concentration of Methotrexate (SIGMA) from 1 nM to 500 nM. Once stable pool was ready then a stable single cell clone was selected for each cell line by limiting dilution with a objective of high producer clone. These clones were banked & stored in vapor phase of Liquid Nitrogen for long uses under GMP conditions.

Experiment set up: Two commercially available chemically define medium were selected to compare the result of universal production medium. Power CHO2 medium was obtained from Lonza (Lonza, Cat#12-770Q) and Medium-D was obtained from Sigma. Each CHO cell line was revived directly in respective medium using standard revival procedures e.g. rapidly thaw the cells in a water bath and decontaminate the vial using 70% ethanol. The cryovial was opened in a class II biological cabinet and cells transfer in a 125 mL of Erlenmeyer shake flasks (obtained from Corning Inc.) containing 20 mL of pre warmed universal production medium and kept it in a 95% humidified CO$_2$ incubator (Climo Shaker ISF4-XC, Kuhner AG, Switzerland) with process condition of 100±5 rpm, 37° C.±1, 5% CO$_2$±2%. This described process condition was maintained throughout the seed development of each cell lines. Once cells reaches to 1-2 millions cells in 1 to 2 days with >95% viability, cells were split in 1:2 ratio by adding 20 mL of fresh complete universal production medium and transfer the culture in a fresh 250 mL of Erlenmeyer shake flask. This step and scale was repeated three times in Power CHO2 medium and Medium-D medium and followed the same procedure as following. Once cells reaches to 3-4 millions cells in 2 to 3 days with >95% viability, cells were passaged by adding 230 mL of fresh complete universal production medium and transfer the culture in a fresh 1 L of Erlenmeyer shake flask. Once cells reaches to 3-4 millions cells in 2 to 3 days with >95% viability, cells were passaged by adding 1250 mL of fresh complete universal production medium and transfer the culture in a fresh 5 L of shake flask, (Obtained from Thomson Instruments).

Glucose was maintained at more than 10 mM by using 2M Glucose stock (Himedia). pH was maintained by 1M sodium bicarbonate buffer stock. Glucose was analyzed by Cedex-Bioanalyzer (Roche). The cell count and viability was analyzed by automated cell counter (Thermo Fisher, Countess II) each day.

It was observed that all cell lineage cell lines reached equal to or more than 20 million cells/mL whereas less than 15 million cells/mL cell density was observed in other commercial medium. (FIGS. 1 to 4).

Example 2

Culturing & expansion of recombinant CHO sub lineage cell lines at 50 L single use bioreactor in universal production medium in batch mode culture.

Recombinant Darbepoetin and Erythropoietin stable cell lines, (described in Example 1), was used to conduct the experiment for Example 2. Revival, seed development, bioreactor process, medium, feeds and condition were kept the same for both the product.

Each cell line was revived directly using standard revival procedures e.g. rapidly thaw the cells in a water bath, decontaminate the vial using 70% ethanol. The cryovial was opened in a class II biological cabinet and cells transfer in a 125 mL of Erlenmeyer shake flasks (Corning Inc.) containing 20 mL of pre warmed universal production medium and kept it in a 95% humidified CO$_2$ incubator (Climo Shaker ISF4-XC, Kuhner AG, Switzerland) with process condition of 100±5 rpm, 37° C.±1, 5% CO$_2$±2%. This described process condition was maintained throughout the seed development of each cell lines. Once cells reaches to 1-2 millions cells in 1 to 2 days with >95% viability, cells were splited in 1:2 ratio by adding 20 mL of fresh complete universal production medium and transfer the culture in a fresh 250 mL of Erlenmeyer shake flask. Once cells reaches to 3-4 millions cells in 2 to 3 days with >95% viability, cells were passaged by adding 230 mL of fresh complete universal production medium and transfer the culture in a fresh 1 L of Erlenmeyer shake flask. Once cells reaches to 3-4 millions cells in 2 to 3 days with >95% viability, cells were passaged by adding 1250 mL of fresh complete universal production medium and transfer the culture in a fresh 5 L of shake flask, (Obtained from Thomson Instruments). Once cells reaches to 3-4 millions cells in 2 to 3 days with >95% viability, cells were passaged by adding 7500 mL of fresh complete universal production medium and transfer the culture in 6 shake flasks of 5 L (Thomson Instruments). Once cells reaches to 3-4 millions cells in 2 to 3 days with >95% viability, cells were transfer in a 50 L single use shaken bioreactor, containing 41 liter of fresh complete universal production medium. The running condition of each bioreactor batch was kept same e.g. Speed 70 rpm±5, pH-7.0-7.2, Temperature 37° C.±1° C., and gas flow rate 0.01 vvm. The glucose was maintained more than 10 mM in the bioreactor by using 2M Glucose (Himedia). pH was maintained by 1M sodium bi carbonate which was connected with control loop of Bioreactor. The Glucose was analyzed by CedexBioanalyzer (Roche). The cell count and viability was analyzed by automated cell counter (Thermo Fisher, Countess II) each day. The doubling time and specific growth rate of cells was calculated based on formula mentioned below and computed in Table 8.

The specific growth rate (μ) was calculated from a semi-log plot of viable cell concentration versus culture time in the exponential growth phase by the following formula:

μ=(ln X2−ln X1)/t2−t1 with X1 and X2 being the viable cell concentrations at time points t1 and t2.

Further Doubling time was calculated by following formula:

Doubling Time=0.693/μ, where μ is the specific growth rate.

It was observed that doubling time was between 15 hours to 18 hours among the sub lineage cell lines and cell density reaches to 20 to 25 million cells/mL ranges (FIG. 5). The viability was well maintained above 90% among the all lineage cells up to 7 days (FIG. 6).

Example 3

Combinatory effects of medium components for improving glycosylation of therapeutic recombinant protein expressed in recombinant CHO sub cell lineage cells at shake flask scale.

Recombinant Erythropoietin stable cell lines, (described in Example 1), was used to conduct the experiment for Example 3. Revival, seed development, feeds and condition were kept the same.

Experiment Set up: Components were selected from Table 5 and were grouped as followed:

| | |
|---|---|
| Group 1, Sugars | Galactose, Mannose, N-acetyl-D-Mannosamine, Glucosamine. |
| Group 2, Trace Element | Manganese sulfate H$_2$O, manganous chloride, ferric nitrate 9H$_2$O, ferrous sulfate 7H$_2$O, ferric ammonium citrate, magnesium chloride anhydrous, magnesium sulfate anhydrous. |
| Group 3, Nucleosides | Uridine, Cytidine. |

A statistical design of experiments (DOE) of all three groups was set up to test their effects on recovery of glycosylated protein after purification. Each group was formulated at a defined concentration in 8 different combinations in a pre universal medium which also is a control medium. A feeding strategy was used to feed the culture daily with 1% Feed A (GE Health care) and 0.2% Feed B (GE Health care) from day 3 onwards till the harvesting for sustaining the peak cell density for longer period of time for higher productivity. The glucose was maintained above 2 g/L and pH was recorded each day and maintained to 7.2. Glucose was analyzed by Cedex Bioanalyzer (Roche). Cell count and viability were analyzed by automated cell counter (Thermo Fisher, Countess II) each day (Dye Exclusion method).

The culture was harvested on day 14 with viability of ≥70%. Harvested culture was centrifuged at 5000 rpm±100, 15 minutes±5, at room temperature to remove the cell mass from the harvest. To further reduce the bio burden from the unprocessed bulk harvest, bulk is filtered through 0.3 μM pore size, "single use Sartoclear P" filter (Sartorius AG). Quantification of Erythropoietin alfa was calculated by rp-HPLC developed and validated by Nanogen. Filtered bulk was purified by sequential steps of chromatography of blue sepharose 6 fast, followed by desalting and anion exchange chromatography (DEAE sepharose fast flow, GE healthcare). Acidic form of Erythropoietin alfa was eluted with low pH acetate buffer with pH 4.5 with 50 mM sodium chloride on anion exchange chromatography. Samples were concentrated with 10 kda centrifugal device (Nanosep 10K Omega, Pall Life sciences) to 1 mg/mL. Isomers were analyzed with respective Innovator drug sample on Iso Electro focusing electrophoresis with 3-6 pH ampholytes gel for Erythropoietin.

It has been observed that the improvement of recovery after anion exchange was unexpected and significant when all these three group's components were present in medium (FIG. 7).

Example 4

Combinatory effects of triple buffers for improving glycosylation of therapeutic recombinant protein expressed in recombinant CHO sub cell lineage cells at shake flask scale.

Recombinant Erythropoietin stable cell lines, (described in Example 1), was used to conduct the experiment for Example 4. Revival, seed development, medium, feeds and condition were kept the same as Example 3. Medium formulation selected from Example 3 was further improved by optimizing the buffering conditions. Three buffers systems were selected and their combinations were tested. Cell growth, harvesting and purification were conducted in the same manner as described in Example 3.

The triple buffer system was observed to maintain good pH level and improved the recovery of glycosylated products significantly (FIG. 8).

Example 5

Comparability study of universal production medium with commercially available medium (% of Recovery of low pI isomers after purification as an indicator) at shake flask scale in fed-batch culture.

Experiment set up: Two commercially available chemically define medium were selected to compare the result of Nanogen universal production medium. Power CHO2 medium was obtained from Lonza (Lonza, Cat#12-770Q) and Medium-D was obtained from Sigma.

Recombinant Darbepoetin and Erythropoietin stable cell lines, (described in Example 1), was used to conduct the experiment for Example 5. Revival, seed development, feeds and condition, harvesting procedure, purification procedure, method of protein analyzing were kept the same as described in Example 3.

It has been observed that universal production medium outperformed among commercially available medium with more than 20% recovery in case of recombinant Erythropoietin and about 15% recovery in case of recombinant Darbepoetin protein whereas both commercially medium were not able to recover more than 6% protein in both the cases (FIG. 9 and FIG. 10).

Example 6

Verification of improved glycosylation of therapeutic recombinant protein expressed in recombinant CHO sub cell lineage cells in universal production medium at 50 L Bioreactor scale.

Recombinant Darbepoetin and Erythropoietin stable cell lines, (described in Example 1), was used to conduct the experiment for Example 6. Revival, seed development, bioreactor process, medium, feeds and condition were kept the same for both the product. Cells were revived separately but directly using standard revival procedures e.g. rapidly thaw the cells in a water bath, decontaminate the vial using 70% ethanol. The cryovial was opened in a class II biological cabinet and cells transfer in a 125 mL of Erlenmeyer shake flasks (obtained from Corning Inc.) containing 20 mL of pre warmed universal production medium and kept it in a 95% humidified $CO_2$ incubator (Climo Shaker ISF4-XC, Kuhner AG, Switzerland) with process condition of 100±5 rpm, 37° C.±1, 5% $CO_2$±2%. This described process condition was maintained throughout the seed development of each cell lines. Once cells reaches to 1-2 millions cells in 1 to 2 days with >95% viability, cells were divided in 1:2 ratio by adding 20 mL of fresh complete universal production medium and transfer the culture in a fresh 250 mL of Erlenmeyer shake flask. Once cells reaches to 3-4 millions cells in 2 to 3 days with >95% viability, cells were passaged by adding 230 mL of fresh complete universal production medium and transfer the culture in a fresh 1 L of Erlenmeyer shake flask. Once cells reaches to 3-4 millions cells in 2 to 3 days with >95% viability, cells were passaged by adding 1250 mL of fresh complete universal production medium and transfer the culture in a fresh 5 L of shake flask, (Thomson Instruments). Once cells reaches to 3-4 millions cells in 2 to 3 days with >95% viability, cells were passaged by adding 6000 mL of fresh complete universal production medium and transfer the culture in 5 shake flasks of 5 L (Thomson Instruments). Once cells reaches to 3-4 millions cells in 2 to 3 days with >95% viability, cells were transfer in a 50 L single use shaken bioreactor, containing 32.5 liter of fresh complete universal production medium. The running condition of each bioreactor batch was kept same e.g. Speed 70 rpm±5, pH-7.0-7.2, Temperature 37° C.±1° C., and gas flow rate 0.01 vvm. The glucose was maintained more than 10 mM in the bioreactor by using 2M Glucose (Himedia) throughout the process. pH was maintained by 1M sodium bi carbonate which was connected with control loop of Bioreactor. A feeding strategy was used to feed the culture daily with 1% Feed A (GE Health care) and 0.2% Feed B (GE Health care) from day 3 onwards till the harvesting for sustaining the peak cell density for longer period of time for higher productivity. Growth profile of both the cell line was shown in FIG. 11. The cell mass reaches to 20 to 25 million cells/mL ranges. The medium and process condition was able to sustain the peak cell density to 5 to 7 days with viability above the 85%±5% (FIG. 10). The osmolality was maintained in range of 280 to 380 mOsm (FIG. 12), glucose was maintained above 2 g/L (FIG. 13). The pH fluctuation profile was within the range of ±0.1 from the set point of 7.2 with maintenance of the osmolality less than 380 mOsm, (FIG. 14). The Glucose was analyzed by Cedex Bioanalyzer (Roche). Osmolality was analyzed by Osmo meter (Model 2020, Advance Instruments Inc.). The cell count and viability was analyzed by automated cell counter (Thermo Fisher, Countess II) each day (Dye Exclusion method).

The culture was harvested on day 14 with viability of ≥70%. Harvested culture was centrifuged at 5000 rpm±100, 15 minutes±5, room temperature to remove the cell mass from the harvest. Further, to remove the colloidal particles, cell debris, cell membrane particles, or in particularly, more than 1 micron size particles, cell clarified culture was filtered through with depth filter (25 $cm^2$ surface area, 1 µM pore size, "single use Sartoclear P" depth filter, Sartorius AG) at 15 L/h flux rate, pressure 0.2 bar. Further to reduce the bio burden from the unprocessed bulk harvest, bulk is filtered through 25 $cm^2$ surface area, 0.3 µM pore size, "single use Sartoclear P" depth filter (Sartorius AG) at 10 L/h flux rate, pressure 0.2 bar.

Quantification of Erythropoietin alfa and Darbepoetin alfa protein was calculated by rp-HPLC developed and validated by Nanogen. Filtered bulk was purified by sequential steps of chromatography of blue sepharose 6 fast, followed by desalting and anion exchange chromatography (DEAE sepharose fast flow, GE healthcare). Acidic form of Erythropoietin alfa and Darbepoetin alfa was eluted with low pH acetate buffer with pH 4.5 with 50 mM sodium chloride on anion exchange chromatography. Recovery was calculated (FIG. 15). Samples were concentrated with 10 kda centrifugal device (Nanosep 10K Omega, Pall Life sciences) to 1 mg/mL. Isomers were analyzed with respective Innovator drug sample on Iso Electro focusing electrophoresis (gel, 2-4 pH ampholytes for Darbepoetin and 2-6 pH ampholytes gel for Erythropoietin).

Perfect comparability of isomer with respect to Innovator Drug was observed on IEF gel for both the products, Image. 1 and Image. 2.

Example 7

Comparability of Nanogen universal medium performance with commercially available medium (Productivity as an Indicator) of therapeutic recombinant protein expressed in recombinant CHO sub cell lineage cells at 50 L scale.

Recombinant Etanercept stable cell lines, (described in Example 1), was used to conduct the experiment for Example 7. Two commercially available chemically define medium were selected to compare with the result of the universal production medium. Power CHO2 medium (Lonza, Cat#12-770Q) were obtained from Lonza and Medium-D were obtained from Sigma. Revival, seed development, bioreactor process, medium, feeds and run condition, harvesting and cell clarification method were identical to Examples 2 and 6. Purification of Etanercept was carried out with Protein-A affinity resign (obtained from GE healthcare) and eluted with 20 mM citrate buffer pH 3.5. Sample were dialyzed with 50 mM phosphate buffer pH 7.2 and analyzed on rp-HPLC method.

It has been observed that productivity in universal medium is significantly higher than other medium and reached to 3 g/L analyzed by rp-HPLC method (FIG. 16).

Example 8

Universal Production Medium performance in perfusion culture.

Recombinant Erythropoietin stable cell lines, (described in Example 1), was used to conduct the experiment for Example 8. Cells were revived directly using standard revival procedures e.g. rapidly thaw the cells in a water bath, decontaminate the vial using 70% ethanol. The cryovial was opened in a class II biological cabinet and cells transfer in a 125 mL of Erlenmeyer shake flasks (obtained from Corning Inc.) containing 20 mL of pre warmed universal production medium and kept it in a 95% humidified $CO_2$ incubator (Climo Shaker ISF4-XC, Kuhner AG, Switzerland) with process condition of 100±5 rpm, 37° C.±1, 5% $CO_2$±2%. This described process condition was maintained throughout the seed development of each cell lines. Once cells reach to 1-2 millions cells in 1 to 2 days with >95% viability, cells were divided in 1:2 ratio by adding 20 mL of fresh complete universal production medium and transfer the culture in a fresh 250 mL of Erlenmeyer shake flask. Once cells reaches to 3-4 millions cells in 2 to 3 days with >95% viability, cells were passaged by adding 230 mL of fresh complete universal production medium and transfer the culture in a fresh 1 L of Erlenmeyer shake flask. Once cells reaches to 3-4 millions cells in 2 to 3 days with >95% viability, cells were passaged by adding 1250 mL of fresh complete universal production medium and transfer the culture in a fresh 5 L of shake flask, (Thomson Instruments). The packed-bed basket impeller, combined with Fibra-Cel® disks in 14 L glass bioreactor (New Brunswick) was assembled as supplier instruction. It consists of a basket, with two horizontally positioned, perforated metal screens, filled with 200 grams of Fibra-Cel disks in between that. Fibra-Cel is a solid supported fiber mesh to entrap the cells and allow them to grow. The impeller consists of a hollow tube (draft tube) with three smaller discharge tubes radiating from the top. Once cells reaches to 3-4 millions cells in 2 to 3 days with >95% viability, cells were transfer into this bioreactor containing 8.5 liter of fresh complete universal production medium. The running condition of bioreactor batch was Speed 80 rpm±5, pH-7.0-7.2, Temperature 37° C.±1° C., and gas flow rate 0.01 vvm. The glucose was maintained more than 10 mM in the bioreactor by using 2M Glucose (Himedia) throughout the process. pH was maintained by 1M sodium bi carbonate which was connected with control loop of Bioreactor. Full reactor volume medium was perfused every two days from day 1 onwards till the harvesting for sustaining the peak cell density for longer period of time for higher productivity. Cell growth was monitoring with glucose consumption profile. The pH fluctuation profile was within the range of ±0.1 from the set point of 7.2. The Glucose was analyzed by CedexBioanalyzer (Roche). The productivity was monitored by running SDS-PAGE gel electrophoresis method each day. Each harvested culture was clarified and purified as mentioned in Example 5.

Perfect comparability of isomer with Innovator was observed on IEF gel, Image. 3. Increasing productivity of each harvested culture was observed on SDS-PAGE gel, Image. 4.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosures of all documents cited throughout this application are incorporated herein by reference.

Tables 1 to 6: List of components used to formulate cell culture medium (universal production medium.)

Table 7: List of CHO lineage cells and the expressed recombinant therapeutic product, respectively.

Table 8: Specific growth rate and doubling time of CHO lineage cells in a 50 L single use shaken Bioreactor.

TABLE 1

Universal Production Medium Composition.

| Chemical Name | Concentration Range (mg/L) | Concentration Range (mg/L) |
| --- | --- | --- |
| L-Alanine | 23.1-24.1 | 20-25 |
| Glycine | 23.1-24.1 | 20-25 |
| L-ArginineHCl | 425.9-428.9 | 380-460 |
| L-HistidineHCl $H_2O$ | 237.1-241.1 | 210-260 |
| L-Lysine HCl | 575.6-581.5 | 525-625 |
| L-Methionine | 180.6-185.6 | 160-200 |
| L-Proline | 428.9-432.9 | 375-470 |
| L-Serine | 530.6-535.6 | 475-580 |
| L-Threonine | 321.1-325.1 | 290-350 |
| L-Asparagine $H_2O$ | 850.5-856.5 | 775-925 |
| L-Aspartic Acid | 195.7-199.7 | 180-220 |
| L-Cysteine HCl $H_2O$ | 109.7-204.7 | 100-120 |
| L-Cystine2HCl | 60.6-63.6 | 50-70 |
| L-Glutamic Acid | 220.2-224.2 | 200-240 |
| L Hydroxyproline | 104.4-106.4 | 90-115 |
| L-IsoLeucine | 422.6-425.6 | 375-475 |
| L Leucine | 590.6-594.6 | 540-650 |
| L-Valine | 369.5-372.5 | 330-400 |
| L-Phenylalanine | 233.9-236.9 | 210-250 |
| L-Tryptophan | 251.8-254.8 | 230-275 |
| L-Tyrosine Disodium Salt | 254.5-257.5 | 230-275 |

TABLE 2

Universal Production Medium Composition.

| Chemical Name | Concentration Range (mg/L) | Concentration Range (mg/L) |
| --- | --- | --- |
| Niacinamide | 40.1-43.1 | 36-44 |
| D-Calcium Pantothenate | 3.4-3.8 | 3-4 |
| Para Amino Benzoic Acid | 1.1-1.2 | 1.1-1.5 |
| Ascorbic Acid, Mg Salt | 11.4-12.4 | 10-13 |
| Vitamin $B_{12}$ | 13.2-14.2 | 12-15 |
| Pyridoxine HCl | 3.2-5.2 | 2.5-6 |
| Thiamine HCl | 5.1-6.1 | 4.5-7.5 |
| Folic Acid | 21.7-23.7 | 19-25 |
| Biotin | 1.1-1.7 | 1-2 |
| Riboflavin | 0.5-1.2 | 0.45-1.5 |

TABLE 3

Universal Production Medium Composition.

| Chemical Name | Concentration Range (mg/L) | Concentration Range (mg/L) |
| --- | --- | --- |
| Ammonium Meta Vanadate | 0.00136-0.00146 | 0.00120-0.00150 |
| Sodium Meta Vanadate | 0.00126-0.00136 | 0.00110-0.00140 |
| Germanium Dioxide | 0.00054-0.00059 | 0.00045-0.00060 |
| Barium Acetate | 0.00264-0.00274 | 0.00230-0.00290 |
| Aluminum Chloride $6H_2O$ | 0.00122-0.00132 | 0.00110-0.00140 |
| Rubidium Chloride | 0.00142-0.00152 | 0.00130-0.00160 |
| Chromium Sulfate $15H_2O$ | 0.00065-0.00071 | 0.00050-0.00075 |
| Stannous Chloride $2H_2O$ | 0.00023-0.00024 | 0.00020-0.00025 |
| Potassium Bromide | 0.00012-0.00014 | 0.00010-0.00015 |
| Potassium Iodide | 0.00019-0.00023 | 0.00015-0.00025 |
| Silver Nitrate | 0.00018-0.00022 | 0.00015-0.00025 |
| Nickelous Sulfate $6H_2O$ | 0.00027-0.00031 | 0.00024-0.00030 |
| Ammonium Molybdate | 0.01217-0.014 | 0.010-0.015 |
| Cobalt Chloride $6H_2O$ | 0.00976-0.01 | 0.008-0.012 |
| Cupric Sulfate $5H_2O$ | 0.01017-0.012 | 0.010-0.015 |
| Sodium Selenite | 0.03536-0.037 | 0.030-0.040 |
| Cadmium Chloride $2.5H_2O$ | 0.04624-0.049 | 0.040-0.050 |
| Zinc Sulfate | 1.40640-1.48 | 1.25-1.50 |
| Putrescine2HCl | 0.65040-0.7 | 0.5-0.7 |
| Zinc Chloride | 1.80000-1.9 | 1.5-2.0 |

TABLE 3-continued

Universal Production Medium Composition.

| Chemical Name | Concentration Range (mg/L) | Concentration Range (mg/L) |
|---|---|---|
| Cupric Chloride 2H$_2$O | 0.07000-0.09 | 0.05-0.10 |
| Glutathione Reduced | 1.42560-1.52 | 1.2-1.6 |
| Sodium Metasilicate | 0.35760-0.46 | 0.25-0.50 |
| Choline Chloride | 39.10500-42.57 | 35-45 |
| i-Inositol | 46.20429-48.25 | 40-50 |
| Monothioglycerol | 5.97300-6.12 | 5.4-6.5 |
| Ethanolamide | 7.78800-8.2 | 7.0-9.0 |
| 2-Mecaptoethanol | 0.00040-0.0005 | 0.00030-0.00050 |
| Titanium Tetrachloride | 0.00017-0.0002 | 0.00012-0.00020 |
| Sodium Phosphate Dibasic Anhydrous | 238.85400-241.832 | 220-250 |
| Potassium Chloride | 421.21200-426.215 | 350-450 |
| EDTA Tetra Sodium Salt Dihydrate | 2.21100-2.32 | 2.0-2.5 |
| Calcium Chloride Anhydrous | 11.10000-13.4 | 10-15 |
| Spermine | 3.00300-4.3 | 2-5 |
| 2 Hydroxy Pyridine N Oxide | 1.98000-2.35 | 1.5-3.0 |

TABLE 4

Universal Production Medium Composition

| Chemical Name | Concentration Range (mg/L) | Concentration Range (mg/L) |
|---|---|---|
| Adenosine | 10-11 | 8-15 |
| Deoxyadenosine | 10-12 | 8-15 |
| Deoxycytidine | 10-12 | 8-15 |
| Deoxyguanosine | 10-12 | 8-15 |
| Guanosine | 10-13 | 8-15 |
| D-Glucose (Dextrose) | 4000-6000 | 3000-10000 |
| Sodium Pyruvate | 110-119 | 90-130 |
| L-Glutamine | 2920-3140 | 2500-3500 |
| PluronicF68 | 1000-1150 | 800-1200 |
| Sodium Chloride | 3500-3850 | 3000-4000 |

TABLE 5

Universal Production Medium Composition.

| Chemical Name | Concentration Range (mg/L) | Concentration Range (mg/L) |
|---|---|---|
| D-Mannitol | 100-115 | 80-120 |
| D-Galactose | 270-290 | 250-300 |
| D-Mannose | 270-297 | 250-300 |
| N-Acetyl-D-Mannosamine | 90-95 | 80-100 |
| Glucosamine | 215.6-221 | 200-225 |
| Manganese Sulfate H$_2$O | 0.00010-0.0002 | 0.00010-0.0005 |
| Manganous Chloride | 0.00007-0.0001 | 0.00007-0.0002 |
| Nickelous Chloride 6H$_2$O | 0.00008-0.0001 | 0.00008-0.0002 |
| Ferric Nitrate 9H$_2$O | 1.28400-1.34 | 1.1-1.4 |
| Ferrous Sulfate 7H$_2$O | 3.98400-4.45 | 3.0-5.0 |
| Ferric Ammonium Citrate | 1.57200-1.68 | 1.4-1.7 |
| Magnesium Chloride Anhydrous | 73.32600-75.7 | 65-80 |
| Magnesium Sulfate Anhydrous | 15.90600-17.4 | 12-18 |
| Cytidine | 20-20.5 | 18-22 |
| Uridine | 20-21.5 | 18-22 |

TABLE 6

Universal Production Medium Composition.

| Chemical Name | Concentration Range (mg/L) | Concentration Range (mg/L) |
|---|---|---|
| Sodium carbonate | 1500-1700 | 1200-1800 |
| Sodium bi carbonate | 2200-2350 | 2000-2500 |
| HEPES | 2380-2470 | 2000-2500 |

TABLE 7

Recombinant CHO sub lineage cells.

| Cell Type | Protein Name | Protein Class | Clinical Indication |
|---|---|---|---|
| CHOK1 | Trastuzumab | Humanized Antibody | Breast Cancer |
| CHO-S | Etanercept | Fusion Protein | Rheumatoid Arthritis |
| CHO-DG44 | Erythropoietin | Hormone | Anemia |
| CHO-DUX-B11 | Darbepoetin | Hormone | Anemia |

TABLE 8

Specific Growth Rate and Doubling time.

| Cell Type | Protein Name | Specific Growth Rate (per hour) | Doubling Time (hours) |
|---|---|---|---|
| CHO DG44 | Erythropoietin | 0.039 | 17.58 |
| CHO DUXB11 | Darbepoetin | 0.043 | 16.10 |
| CHOK1 | Trastuzumab | 0.041 | 16.75 |
| CHO-S | Etanercept | 0.046 | 15.19 |

What is claimed is:

1. A cell culture medium for culturing cell lines suitable for producing a therapeutic protein, comprising:
   a) an amino acid selected from a group consisting of L-arginine, L-asparagine, L-proline, L-leucine and L-hydroxyproline, or a mixture thereof;
   b) a vitamin selected from a group consisting of ascorbic acid Mg$^{2+}$ salt, biotin, pyridoxine HCL, folic acid, riboflavin and D-calcium pantothenate, or a mixture thereof;
   c) an element selected from a group consisting of ammonium meta vanadate, sodium meta vanadate, germanium dioxide, barium acetate, aluminum chloride, rubidium chloride, cadmium chloride, ammonium molybedate, stannous chloride, cobalt chloride, chromium sulfate, silver nitrate, sodium metasilicate, zinc sulfate, manganese sulfate H$_2$O, manganous chloride, ferric nitrate 9H$_2$O, ferrous sulfate 7H$_2$O, ferric ammonium citrate, magnesium chloride anhydrous, and magnesium sulfate anhydrous, or a mixture thereof;
   d) a nucleoside selected from a group consisting of uridine and cystidine, or a mixture thereof;
   e) a sugar selected from a group consisting of galactose, mannose and N-acetyl-D-mannosamine, or a mixture thereof; and
   f) a triple buffering system comprising sodium carbonate, sodium bicarbonate and HEPES;
wherein the cell culture medium is animal component-free, plant component-free, serum-free, growth factors-free, recombinant protein-free, lipids-free, steroids-free, and free of plant or animal hydrolysates and/or extracts.

2. The cell culture medium according to claim 1, wherein the cell culture medium comprises:
about 350 to about 500 mg/L L-arginine;
about 700 to about 900 mg/L L-asparagine;
about 350 to about 500 mg/L L-proline;
about 500 to about 650 mg/L leucine; and
about 90 to about 110 mg/L hydroxyproline.

3. The cell culture medium according to claim 1, wherein the cell culture medium comprises:
about 8 to about 14mg/L ascorbic acid $Mg^{2+}$ salt;
about 1.0 to about 1.5 mg/L biotin;
about 2.5 to about 4 mg/L pyridoxine HCL;
about 19 to about 23 mg/L folic acid;
about 4 to about 6 mg/L riboflavin; and
about 3 to about 4 mg/L D-calcium pantothenate.

4. The cell culture medium according to claim 1, comprising:
about 1 to about 1.5 µg/L ammonium meta vanadate;
about 1 to about 1.8 µg/L sodium meta vanadate;
about 0.2 to about 0.8 vg/L germanium dioxide;
about 2 to about 3 µg/L barium acetate;
about 1 to about 1.6 µg/L aluminum chloride;
about 1.1 to about 1.7 µg/L rubidium chloride;
about 35 to about 75 µg/L cadmium chloride;
about 5 to about 20 µg/L ammonium molybedate;
about 0.1 to about 0.5 µg/L stannous chloride;
about 5 to about 15 µg/L cobalt chloride;
about 0.1 to about 1 µg/L chromium sulfate;
about 0.1 to about 0.2 µg/L silver nitrate;
about 200 to about 600 µg/L sodium metasilicate; and
about 100 to about 600 µg/L zinc sulfate.

5. The cell culture medium according to claim 1, comprising:
about 15 to about 25 mg/L Uridine; and
about 18 to about 25 mg/L Cytidine.

6. The cell culture medium according to claim 1, comprising:
about 0.1 to about 0.9 mg/L manganese sulfate $H_2O$;
about 0.1 to about 0.5 mg/L manganous chloride;
about 0.3 to about 2 mg/L ferric nitrate $9H_2O$;
about 2 to about 5 mg/L ferrous sulfate $7H_2O$;
about 1 to about 2.5 mg/L ferric ammonium citrate;
about 40 to about 100 mg/L magnesium chloride anhydrous; and
about 10 to about 20 mg/L magnesium sulfate anhydrous.

7. The cell culture medium according to claim 1, comprising:
about 100 mg to about 500 mg/L galactose;
about 100 to about 500 mg/L mannose;
about 50 to about 150 mg/L N-Acetyl-D-Mannosamine; and
about 100 to 300 mg/L glucosamine.

8. The cell culture medium according to claim 1, wherein the cell culture medium comprises the triple buffering system comprising:
about 1.5 g/L sodium carbonate;
about 2.2 g/L sodium bi carbonate; and
about 2.38 g/L HEPES.

9. The cell culture medium according to claim 1, wherein the cell culture medium is capable of growing the cell lines at a cell density of more than 20 million cells/mL.

10. The cell culture medium according to claim 1, wherein the cell culture medium is used to grow the cell lines in a batch, fed-batch, or perfusion mode culture without the need of cell clone adaptation.

11. The cell culture medium according to claim 1, wherein the cell culture medium enhances glycosylation of therapeutic protein by about 20% to about 200%.

12. The cell culture medium according to claim 1, wherein the cell culture medium enhances glycosylation of therapeutic protein by about 20%, 30%, 40%, 50%, 60%, 70%, 80%, 100%, 120%, 130%, 140%, 150%, 160%, 170%, 180%, 190% and 200%.

13. The cell culture medium according to claim 1, wherein the cell culture medium increases the expression of recombinant proteins in a fed-batch mode culture by about 5%, 10%, 20%, 30%, 40%, 50%, 60%, 70%, 80%, 90%, 100%, 120%, 130%, 140%, 150%, 160%, 170%, 180%, 190% and 200%.

14. The cell culture medium according to claim 1, wherein the cell culture medium is useful in commercial manufacturing of therapeutic proteins.

15. A kit for culturing CHO cell lines suitable for producing a therapeutic protein, comprising a cell culture medium according to claim 1.

* * * * *